United States Patent
Aster et al.

(10) Patent No.: US 8,062,315 B2
(45) Date of Patent: Nov. 22, 2011

(54) VARIABLE PARIETAL/VISCERAL PLEURAL COUPLING

(75) Inventors: Walter J. Aster, Brentwood, CA (US); Asia Chang, Los Angeles, CA (US); Don Tanaka, Saratoga, CA (US)

(73) Assignee: Portaero, Inc., Cupertino, CA (US)

( * ) Notice: Subject to any disclaimer, the term of this patent is extended or adjusted under 35 U.S.C. 154(b) by 846 days.

(21) Appl. No.: 12/030,006

(22) Filed: Feb. 12, 2008

(65) Prior Publication Data
US 2008/0287973 A1 Nov. 20, 2008

Related U.S. Application Data

(60) Provisional application No. 60/938,466, filed on May 17, 2007.

(51) Int. Cl.
*A61B 17/08* (2006.01)
(52) U.S. Cl. ........................................................ 606/153
(58) Field of Classification Search .......... 606/153–156, 606/215–216; 24/303; 604/264, 288.01–288.02; 128/207.14; 248/467
See application file for complete search history.

(56) References Cited

U.S. PATENT DOCUMENTS

| | | | |
|---|---|---|---|
| 733,152 A * | 7/1903 | Chisholm | |
| 953,922 A * | 4/1910 | Rogers | |
| 2,206,687 A * | 7/1940 | Bloomheart | |
| 2,867,213 A * | 1/1959 | Thomas, Jr. | |
| 2,873,742 A * | 2/1959 | Shelden | |
| 2,991,787 A * | 7/1961 | Shelden et al. | |
| 3,253,594 A * | 5/1966 | Matthews et al. | |
| 3,294,355 A * | 12/1966 | Topf | 248/467 |
| 3,384,087 A * | 5/1968 | Brummelkamp | |
| 3,463,159 A * | 8/1969 | Heimlich | |
| 3,511,243 A * | 5/1970 | Toy | |
| 3,556,103 A * | 1/1971 | Calhoun et al. | |
| 3,638,649 A * | 2/1972 | Ersek | |
| 3,682,166 A * | 8/1972 | Jacobs | |
| 3,688,773 A * | 9/1972 | Weiss | |
| 3,777,757 A * | 12/1973 | Gray et al. | 604/99.04 |
| 3,788,326 A * | 1/1974 | Jacobs | |
| 3,817,250 A * | 6/1974 | Weiss et al. | |
| 3,908,704 A * | 9/1975 | Clement et al. | |
| 3,916,903 A * | 11/1975 | Pozzi | |
| 4,153,058 A * | 5/1979 | Nehme | |
| 4,291,694 A * | 9/1981 | Chai | 604/512 |
| 4,439,189 A * | 3/1984 | Sargeant et al. | |
| 4,465,062 A * | 8/1984 | Versaggi et al. | |

(Continued)

FOREIGN PATENT DOCUMENTS
EP 0260543 A1 3/1988
(Continued)

OTHER PUBLICATIONS

Al-Salem et al., "Computed tomography-guided percutaneous needle aspiration of lung abscesses in neonates and children", Pediatr Surg Int (1997) 12: 417-419, copyright Springer-Verlag 1997.

(Continued)

*Primary Examiner* — Melanie Tyson
*Assistant Examiner* — Son Dang
(74) *Attorney, Agent, or Firm* — Fliesler Meyer LLP

(57) ABSTRACT

A variable parietal/visceral pleural coupling may be utilized to create an air-tight seal in the pleural space between the parietal and visceral pleura. This coupling may be utilized to create a seal for other implantable devices.

18 Claims, 13 Drawing Sheets

U.S. PATENT DOCUMENTS

| | | | |
|---|---|---|---|
| 4,502,482 A * | 3/1985 | DeLuccia et al. | |
| 4,583,977 A * | 4/1986 | Shishov et al. | |
| 4,664,660 A | 5/1987 | Goldberg et al. | |
| 4,705,039 A * | 11/1987 | Sakaguchi et al. | 606/154 |
| 4,799,494 A | 1/1989 | Wang | |
| 4,813,929 A | 3/1989 | Semrad | |
| 4,826,495 A | 5/1989 | Petersen | |
| 4,828,553 A | 5/1989 | Nielsen | |
| 4,869,717 A | 9/1989 | Adair | |
| 4,872,869 A | 10/1989 | Johns | |
| 4,889,534 A | 12/1989 | Mohiuddin et al. | |
| 4,905,694 A * | 3/1990 | Will | 606/217 |
| 4,931,045 A | 6/1990 | Steer | |
| 4,944,724 A | 7/1990 | Goldberg et al. | |
| 4,959,054 A | 9/1990 | Heimke et al. | |
| 4,976,688 A | 12/1990 | Rosenblum | |
| 5,004,456 A | 4/1991 | Botterbusch et al. | |
| 5,060,645 A | 10/1991 | Russell | |
| 5,073,169 A * | 12/1991 | Raiken | 604/180 |
| 5,078,689 A | 1/1992 | Keller | |
| 5,137,509 A | 8/1992 | Freitas | |
| 5,139,485 A | 8/1992 | Smith et al. | |
| 5,141,516 A * | 8/1992 | Detweiler | 606/154 |
| 5,218,957 A | 6/1993 | Strickland | |
| 5,230,332 A | 7/1993 | Strickland | |
| 5,230,350 A | 7/1993 | Fentress | |
| 5,261,708 A * | 11/1993 | Steer | 285/319 |
| 5,263,939 A | 11/1993 | Wortrich | |
| 5,312,331 A | 5/1994 | Knoepfler | |
| 5,315,992 A | 5/1994 | Dalton | |
| 5,336,206 A | 8/1994 | Shichman | |
| 5,354,283 A | 10/1994 | Bark et al. | |
| 5,356,386 A | 10/1994 | Goldberg et al. | |
| 5,366,478 A * | 11/1994 | Brinkerhoff et al. | 606/213 |
| 5,370,625 A | 12/1994 | Shichman | |
| 5,376,376 A | 12/1994 | Li | |
| 5,389,077 A | 2/1995 | Melinyshyn et al. | |
| 5,401,262 A | 3/1995 | Karwoski et al. | |
| 5,407,433 A * | 4/1995 | Loomas | 604/167.06 |
| 5,431,633 A | 7/1995 | Fury | |
| 5,478,333 A | 12/1995 | Asherman, Jr. | |
| 5,484,401 A | 1/1996 | Rodriguez et al. | |
| 5,496,297 A | 3/1996 | Olsen | |
| 5,501,677 A | 3/1996 | Jensen | |
| 5,501,678 A | 3/1996 | Olsen | |
| 5,588,424 A | 12/1996 | Insler et al. | |
| 5,616,131 A | 4/1997 | Sauer et al. | |
| 5,660,175 A | 8/1997 | Dayal | |
| 5,662,629 A | 9/1997 | Steer et al. | |
| 5,728,066 A | 3/1998 | Daneshvar | |
| 5,730,735 A | 3/1998 | Holmberg et al. | |
| 5,738,661 A | 4/1998 | Larice | |
| 5,807,341 A | 9/1998 | Heim | |
| 5,830,200 A | 11/1998 | Steer et al. | |
| 5,843,053 A | 12/1998 | Steer | |
| 5,897,531 A | 4/1999 | Amirana | |
| 5,931,821 A | 8/1999 | Weilbacher et al. | |
| 5,954,636 A | 9/1999 | Schwartz et al. | |
| 5,961,090 A * | 10/1999 | Parkin | 248/475.1 |
| 5,971,962 A | 10/1999 | Kojima et al. | |
| 5,972,026 A | 10/1999 | Laufer et al. | |
| 5,991,980 A * | 11/1999 | Meager | 24/400 |
| 6,059,816 A | 5/2000 | Moenning | |
| 6,083,255 A | 7/2000 | Laufer et al. | |
| 6,174,323 B1 | 1/2001 | Biggs et al. | |
| 6,197,010 B1 | 3/2001 | Leise, Jr. et al. | |
| 6,200,333 B1 | 3/2001 | Laufer | |
| 6,258,100 B1 | 7/2001 | Alferness et al. | |
| 6,273,907 B1 | 8/2001 | Laufer | |
| 6,283,988 B1 | 9/2001 | Laufer et al. | |
| 6,283,989 B1 | 9/2001 | Laufer et al. | |
| 6,287,290 B1 | 9/2001 | Perkins et al. | |
| 6,293,930 B1 | 9/2001 | Brunsgaard et al. | |
| 6,293,951 B1 | 9/2001 | Alferness et al. | |
| 6,299,633 B1 | 10/2001 | Laufer | |
| 6,322,536 B1 | 11/2001 | Rosengart et al. | |
| 6,328,689 B1 | 12/2001 | Gonzalez et al. | |
| 6,330,882 B1 | 12/2001 | French | |
| 6,334,441 B1 | 1/2002 | Zowtiak et al. | |
| 6,358,269 B1 | 3/2002 | Aye | |
| 6,398,775 B1 | 6/2002 | Perkins et al. | |
| 6,402,754 B1 | 6/2002 | Gonzalez | |
| 6,411,852 B1 | 6/2002 | Danek et al. | |
| 6,416,554 B1 | 7/2002 | Alferness et al. | |
| 6,432,100 B1 | 8/2002 | Affeld | |
| 6,443,156 B1 | 9/2002 | Niklason et al. | |
| 6,468,292 B1 | 10/2002 | Mollenauer et al. | |
| 6,485,407 B2 | 11/2002 | Alferness et al. | |
| 6,488,673 B1 | 12/2002 | Laufer et al. | |
| 6,491,706 B1 | 12/2002 | Alferness et al. | |
| 6,514,290 B1 | 2/2003 | Loomas | |
| 6,517,519 B1 | 2/2003 | Rosen et al. | |
| 6,520,183 B2 | 2/2003 | Amar | |
| 6,527,761 B1 | 3/2003 | Soltesz et al. | |
| 6,550,475 B1 | 4/2003 | Oldfield | |
| 6,569,121 B1 | 5/2003 | Purow et al. | |
| 6,569,166 B2 | 5/2003 | Gonzalez | |
| 6,585,639 B1 | 7/2003 | Kotmel et al. | |
| 6,589,161 B2 | 7/2003 | Corcoran | |
| 6,592,594 B2 | 7/2003 | Rimbaugh et al. | |
| 6,599,311 B1 | 7/2003 | Biggs et al. | |
| 6,609,521 B1 | 8/2003 | Belani et al. | |
| 6,629,951 B2 | 10/2003 | Laufer et al. | |
| 6,632,239 B2 | 10/2003 | Snyder et al. | |
| 6,632,243 B1 | 10/2003 | Zadno-Azizi et al. | |
| 6,634,360 B1 | 10/2003 | Flodin | |
| 6,634,363 B1 | 10/2003 | Danek et al. | |
| 6,638,253 B2 | 10/2003 | Breznock | |
| 6,653,525 B2 | 11/2003 | Ingenito et al. | |
| 6,659,961 B2 | 12/2003 | Robinson | |
| 6,679,264 B1 | 1/2004 | Deem et al. | |
| 6,682,506 B1 | 1/2004 | Navarro | |
| 6,692,494 B1 | 2/2004 | Cooper et al. | |
| 6,694,979 B2 | 2/2004 | Deem et al. | |
| 6,695,791 B2 | 2/2004 | Gonzalez | |
| 6,709,401 B2 | 3/2004 | Perkins et al. | |
| 6,712,812 B2 | 3/2004 | Roschak et al. | |
| 6,736,797 B1 | 5/2004 | Larsen et al. | |
| 6,749,606 B2 | 6/2004 | Keast et al. | |
| 6,770,063 B2 | 8/2004 | Goldberg et al. | |
| 6,770,070 B1 | 8/2004 | Balbierz | |
| 6,790,172 B2 | 9/2004 | Alferness et al. | |
| 6,827,086 B2 | 12/2004 | Shuman | |
| 6,837,906 B2 | 1/2005 | Ginn | |
| 6,840,243 B2 | 1/2005 | Deem et al. | |
| 6,843,767 B2 | 1/2005 | Corcoran et al. | |
| 6,846,292 B2 | 1/2005 | Bakry | |
| 6,849,061 B2 | 2/2005 | Wagner | |
| 6,852,108 B2 | 2/2005 | Barry et al. | |
| 6,860,847 B2 | 3/2005 | Alferness et al. | |
| 6,878,141 B1 | 4/2005 | Perkins et al. | |
| 6,886,558 B2 * | 5/2005 | Tanaka | 128/200.26 |
| 6,901,927 B2 | 6/2005 | Deem et al. | |
| 6,904,909 B2 | 6/2005 | Andreas et al. | |
| 6,905,518 B2 | 6/2005 | Ginn | |
| 6,916,310 B2 | 7/2005 | Sommerich | |
| 6,929,637 B2 | 8/2005 | Gonzalez et al. | |
| 6,941,950 B2 | 9/2005 | Wilson et al. | |
| 6,997,189 B2 | 2/2006 | Biggs et al. | |
| 6,997,918 B2 | 2/2006 | Soltesz et al. | |
| 7,011,094 B2 | 3/2006 | Rapacki et al. | |
| 7,011,314 B2 * | 3/2006 | McFarlane | 277/626 |
| 7,014,628 B2 | 3/2006 | Bousquet | |
| 7,022,088 B2 | 4/2006 | Keast et al. | |
| 7,033,387 B2 | 4/2006 | Zadno-Azizi et al. | |
| 7,036,509 B2 | 5/2006 | Rapacki et al. | |
| 7,086,398 B2 | 8/2006 | Tanaka | |
| 7,100,616 B2 | 9/2006 | Springmeyer | |
| 7,135,010 B2 | 11/2006 | Buckman et al. | |
| 7,141,046 B2 | 11/2006 | Perkins et al. | |
| 7,165,548 B2 | 1/2007 | Deem et al. | |
| 7,172,581 B2 | 2/2007 | Ciok et al. | |
| 7,175,644 B2 | 2/2007 | Cooper et al. | |
| 7,182,772 B2 | 2/2007 | Alferness et al. | |
| 7,186,259 B2 | 3/2007 | Perkins et al. | |
| 7,192,420 B2 * | 3/2007 | Whiteford | |
| 7,195,016 B2 * | 3/2007 | Loyd et al. | |

| | | | |
|---|---|---|---|
| 7,195,017 B2* | 3/2007 | Tanaka | 128/207.14 |
| 7,207,946 B2* | 4/2007 | Sirokman | |
| 7,232,414 B2* | 6/2007 | Gonzalez | |
| 7,244,245 B2* | 7/2007 | Purow et al. | |
| 7,252,086 B2* | 8/2007 | Tanaka | 128/200.26 |
| 7,594,914 B2* | 9/2009 | Luchetti | 606/41 |
| 2001/0025132 A1* | 9/2001 | Alferness et al. | |
| 2001/0041906 A1* | 11/2001 | Gonzalez | |
| 2001/0041932 A1* | 11/2001 | Scholz et al. | |
| 2002/0042564 A1* | 4/2002 | Cooper et al. | |
| 2002/0062120 A1* | 5/2002 | Perkins et al. | |
| 2002/0077593 A1* | 6/2002 | Perkins et al. | |
| 2002/0087153 A1* | 7/2002 | Roschak et al. | |
| 2002/0111619 A1* | 8/2002 | Keast et al. | |
| 2002/0111620 A1* | 8/2002 | Cooper et al. | |
| 2002/0112729 A1* | 8/2002 | DeVore et al. | |
| 2002/0165618 A1* | 11/2002 | Ingenito et al. | |
| 2002/0188171 A1* | 12/2002 | Alferness et al. | |
| 2003/0013935 A1* | 1/2003 | Alferness et al. | |
| 2003/0018344 A1* | 1/2003 | Kaji et al. | |
| 2003/0050648 A1* | 3/2003 | Alferness et al. | |
| 2003/0051733 A1* | 3/2003 | Kotmel et al. | |
| 2003/0055331 A1* | 3/2003 | Kotmel et al. | |
| 2003/0065339 A1* | 4/2003 | Snyder et al. | |
| 2003/0069488 A1* | 4/2003 | Alferness et al. | |
| 2003/0078469 A1 | 4/2003 | Corcoran | |
| 2003/0083542 A1 | 5/2003 | Alferness et al. | |
| 2003/0083671 A1 | 5/2003 | Rimbaugh et al. | |
| 2003/0127090 A1 | 7/2003 | Gifford et al. | |
| 2003/0130593 A1 | 7/2003 | Gonzalez | |
| 2003/0149446 A1 | 8/2003 | Shuman | |
| 2003/0154576 A1* | 8/2003 | Mirharooni | 24/41.1 |
| 2003/0154988 A1 | 8/2003 | DeVore et al. | |
| 2003/0158515 A1 | 8/2003 | Gonzalez et al. | |
| 2003/0163024 A1 | 8/2003 | Corcoran | |
| 2003/0181356 A1 | 9/2003 | Ingenito | |
| 2003/0181922 A1 | 9/2003 | Alferness | |
| 2003/0183235 A1 | 10/2003 | Rimbaugh et al. | |
| 2003/0186904 A1 | 10/2003 | Ruben et al. | |
| 2003/0195385 A1 | 10/2003 | DeVore | |
| 2003/0195511 A1 | 10/2003 | Barry | |
| 2003/0212337 A1 | 11/2003 | Sirokman | |
| 2003/0212412 A1 | 11/2003 | Dillard et al. | |
| 2003/0216730 A1 | 11/2003 | Barry et al. | |
| 2003/0216769 A1 | 11/2003 | Dillard et al. | |
| 2003/0228344 A1 | 12/2003 | Fields et al. | |
| 2003/0233099 A1 | 12/2003 | Danaek et al. | |
| 2004/0010209 A1 | 1/2004 | Sirokman | |
| 2004/0010289 A1 | 1/2004 | Biggs et al. | |
| 2004/0016435 A1 | 1/2004 | Deem et al. | |
| 2004/0024356 A1* | 2/2004 | Tanaka | 604/104 |
| 2004/0031494 A1 | 2/2004 | Danek et al. | |
| 2004/0040555 A1* | 3/2004 | Tanaka | 128/200.24 |
| 2004/0047855 A1 | 3/2004 | Ingenito | |
| 2004/0055606 A1 | 3/2004 | Hendricksen et al. | |
| 2004/0059263 A1 | 3/2004 | DeVore et al. | |
| 2004/0073155 A1 | 4/2004 | Laufer et al. | |
| 2004/0073191 A1 | 4/2004 | Soltesz et al. | |
| 2004/0073201 A1 | 4/2004 | Cooper et al. | |
| 2004/0073241 A1 | 4/2004 | Barry et al. | |
| 2004/0078026 A1 | 4/2004 | Wagner | |
| 2004/0078054 A1 | 4/2004 | Biggs et al. | |
| 2004/0097983 A1 | 5/2004 | Snyder et al. | |
| 2004/0143282 A1 | 7/2004 | Dillard et al. | |
| 2004/0144387 A1 | 7/2004 | Amar | |
| 2004/0158228 A1 | 8/2004 | Perkins et al. | |
| 2004/0167636 A1 | 8/2004 | Dillard et al. | |
| 2004/0173218 A1 | 9/2004 | Yamada et al. | |
| 2004/0200484 A1 | 10/2004 | Springmeyer | |
| 2004/0206349 A1 | 10/2004 | Alferness et al. | |
| 2004/0210248 A1 | 10/2004 | Gordon et al. | |
| 2004/0211412 A1 | 10/2004 | Alferness et al. | |
| 2004/0211434 A1* | 10/2004 | Loomas et al. | 128/898 |
| 2004/0220446 A1 | 11/2004 | Corcoran et al. | |
| 2004/0220556 A1 | 11/2004 | Cooper et al. | |
| 2004/0225254 A1* | 11/2004 | Tanaka et al. | 604/58 |
| 2004/0231674 A1* | 11/2004 | Tanaka | 128/207.14 |
| 2004/0237966 A1* | 12/2004 | Tanaka | 128/207.15 |
| 2004/0243140 A1 | 12/2004 | Alferness et al. | |
| 2004/0244802 A1* | 12/2004 | Tanaka | 128/207.16 |
| 2004/0244803 A1* | 12/2004 | Tanaka | 128/207.16 |
| 2005/0005936 A1 | 1/2005 | Wondka | |
| 2005/0015106 A1 | 1/2005 | Perkins et al. | |
| 2005/0022809 A1 | 2/2005 | Wondka | |
| 2005/0025816 A1* | 2/2005 | Tanaka | 424/445 |
| 2005/0033310 A1 | 2/2005 | Alferness et al. | |
| 2005/0033344 A1 | 2/2005 | Dillard et al. | |
| 2005/0043745 A1 | 2/2005 | Alferness et al. | |
| 2005/0043751 A1 | 2/2005 | Phan et al. | |
| 2005/0043752 A1 | 2/2005 | Phan et al. | |
| 2005/0049615 A1 | 3/2005 | Cooper et al. | |
| 2005/0056292 A1 | 3/2005 | Cooper | |
| 2005/0060041 A1 | 3/2005 | Phan et al. | |
| 2005/0060042 A1 | 3/2005 | Phan et al. | |
| 2005/0060044 A1* | 3/2005 | Roschak et al. | 623/23.65 |
| 2005/0061322 A1 | 3/2005 | Freitag | |
| 2005/0066976 A1 | 3/2005 | Wondka | |
| 2005/0085801 A1 | 4/2005 | Cooper et al. | |
| 2005/0096529 A1 | 5/2005 | Cooper et al. | |
| 2005/0103340 A1 | 5/2005 | Wondka | |
| 2005/0107783 A1 | 5/2005 | Tom et al. | |
| 2005/0131276 A1 | 6/2005 | Alferness et al. | |
| 2005/0137518 A1 | 6/2005 | Biggs et al. | |
| 2005/0137611 A1 | 6/2005 | Escudero et al. | |
| 2005/0137712 A1 | 6/2005 | Biggs et al. | |
| 2005/0137715 A1 | 6/2005 | Phan et al. | |
| 2005/0145253 A1 | 7/2005 | Wilson et al. | |
| 2005/0161040 A1 | 7/2005 | Tanaka | |
| 2005/0166925 A1 | 8/2005 | Wilson et al. | |
| 2005/0171396 A1 | 8/2005 | Pankratov et al. | |
| 2005/0177144 A1 | 8/2005 | Phan et al. | |
| 2005/0178385 A1 | 8/2005 | Dellaca' et al. | |
| 2005/0178389 A1 | 8/2005 | Shaw et al. | |
| 2005/0192526 A1 | 9/2005 | Biggs et al. | |
| 2005/0203483 A1 | 9/2005 | Perkins et al. | |
| 2005/0205097 A1 | 9/2005 | Kyle, Jr. | |
| 2005/0244401 A1 | 11/2005 | Ingenito | |
| 2005/0281797 A1 | 12/2005 | Gong et al. | |
| 2005/0281801 A1 | 12/2005 | Gong et al. | |
| 2005/0281802 A1 | 12/2005 | Gong et al. | |
| 2005/0282748 A1 | 12/2005 | Gong et al. | |
| 2005/0288549 A1 | 12/2005 | Mathis | |
| 2005/0288550 A1 | 12/2005 | Mathis | |
| 2005/0288684 A1 | 12/2005 | Aronson et al. | |
| 2005/0288702 A1 | 12/2005 | McGurk et al. | |
| 2006/0004400 A1 | 1/2006 | McGurk et al. | |
| 2006/0009748 A1 | 1/2006 | Mathis | |
| 2006/0025815 A1 | 2/2006 | McGurk et al. | |
| 2006/0047291 A1 | 3/2006 | Barry | |
| 2006/0076023 A1 | 4/2006 | Rapacki et al. | |
| 2006/0079838 A1 | 4/2006 | Walker et al. | |
| 2006/0095002 A1 | 5/2006 | Soltesz et al. | |
| 2006/0107961 A1* | 5/2006 | Tanaka | 128/207.14 |
| 2006/0116749 A1 | 6/2006 | Willink et al. | |
| 2006/0118125 A1 | 6/2006 | Tanaka | |
| 2006/0118126 A1 | 6/2006 | Tanaka | |
| 2006/0124126 A1 | 6/2006 | Tanaka | |
| 2006/0130830 A1 | 6/2006 | Barry | |
| 2006/0135947 A1 | 6/2006 | Soltesz et al. | |
| 2006/0135984 A1 | 6/2006 | Kramer et al. | |
| 2006/0142672 A1 | 6/2006 | Keast et al. | |
| 2006/0161233 A1 | 7/2006 | Barry et al. | |
| 2006/0162731 A1 | 7/2006 | Wondka et al. | |
| 2006/0206147 A1 | 9/2006 | DeVore et al. | |
| 2006/0212046 A1 | 9/2006 | Pearce et al. | |
| 2006/0212051 A1 | 9/2006 | Snyder et al. | |
| 2006/0235432 A1 | 10/2006 | DeVore et al. | |
| 2006/0235467 A1 | 10/2006 | DeVore | |
| 2006/0264772 A1 | 11/2006 | Aljuri et al. | |
| 2006/0276807 A1 | 12/2006 | Keast et al. | |
| 2006/0280772 A1 | 12/2006 | Roschak et al. | |
| 2006/0280773 A1 | 12/2006 | Roschak et al. | |
| 2006/0283462 A1 | 12/2006 | Fields et al. | |
| 2007/0005083 A1 | 1/2007 | Sabanathan et al. | |
| 2007/0027434 A1 | 2/2007 | Pedersen et al. | |
| 2007/0043350 A1 | 2/2007 | Soltesz et al. | |
| 2007/0051372 A1* | 3/2007 | Tanaka | 128/207.14 |
| 2007/0055175 A1 | 3/2007 | Caro | |

| | | | |
|---|---|---|---|
| 2007/0088300 | A1 | 4/2007 | Cline et al. |
| 2007/0123922 | A1 | 5/2007 | Cooper et al. |
| 2007/0128174 | A1 | 6/2007 | Kleinsek et al. |
| 2007/0142742 | A1 | 6/2007 | Aljuri et al. |
| 2007/0163598 | A1 | 7/2007 | Chang et al. |
| 2007/0185531 | A1 | 8/2007 | Rimbaugh et al. |
| 2007/0186932 | A1 | 8/2007 | Wondka et al. |
| 2007/0186933 | A1 | 8/2007 | Domingo et al. |
| 2008/0295829 | A1* | 12/2008 | Evens .............. 128/202.27 |

FOREIGN PATENT DOCUMENTS

| | | |
|---|---|---|
| EP | 0609950 A1 | 10/1994 |
| RU | 2192185 | 10/2002 |
| WO | WO 88/01879 | 3/1988 |
| WO | WO 90/04982 | 5/1990 |
| WO | WO 99/45990 | 9/1999 |
| WO | WO 99/66975 | 12/1999 |
| WO | WO 00/76577 A1 | 12/2000 |
| WO | WO 01/02042 A1 | 1/2001 |
| WO | WO 01/45568 A1 | 6/2001 |
| WO | WO 02/076279 A2 | 10/2002 |
| WO | WO 02/096325 A1 | 12/2002 |
| WO | WO 03/007821 A1 | 1/2003 |
| WO | WO 03/020338 A2 | 3/2003 |
| WO | WO 03/061480 A1 | 7/2003 |

OTHER PUBLICATIONS

Ball, Jr. et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, Mechanics of the Lung and Respiratory System.

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung Volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

MacKlem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

Rendina et al., "Feasibility and safety of the airway bypass procedure for patients with emphysema", The Journal of Thoracic and Cardiovascular Surgery 2003; 125: 1294-1299.

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e...> May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prostheses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thorac Surg 2006; 82: 2308-2309.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al. "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woolcock et al., "Mechanical factors influencing collateral ventilation in human, dog, and pig lungs", Journal of Applied Physiology 1971, 30: 99-115.

Woodring et al., "Pneumothorax ex vacuo", Chest 1996, 110: 1102-1124.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

* cited by examiner

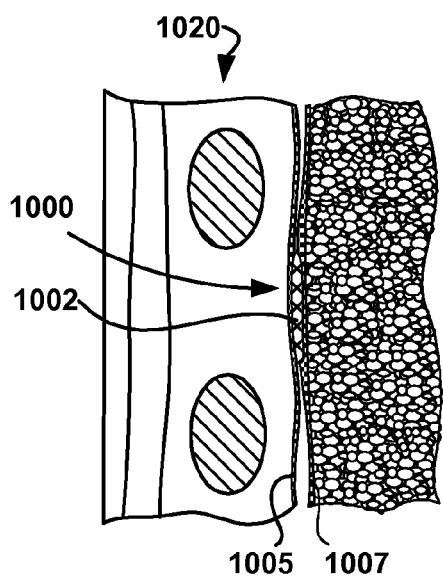
FIG. 10A
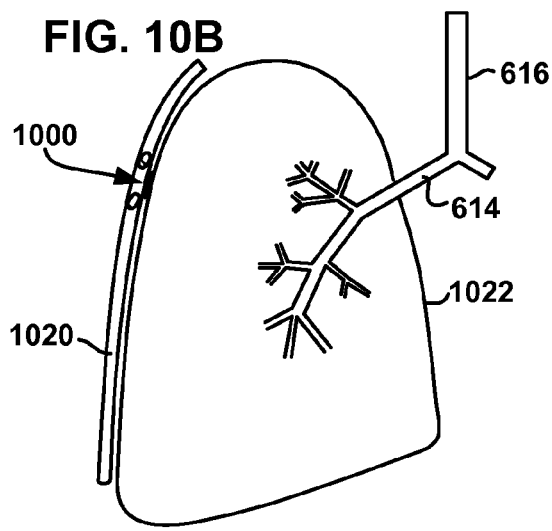
FIG. 10B
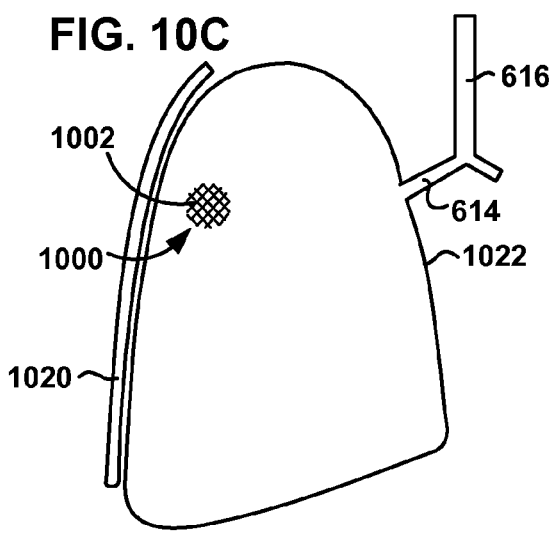
FIG. 10C
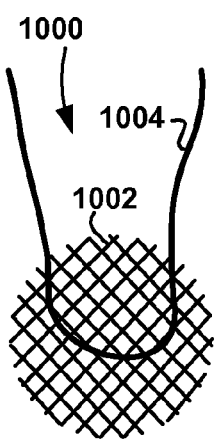
FIG. 10D
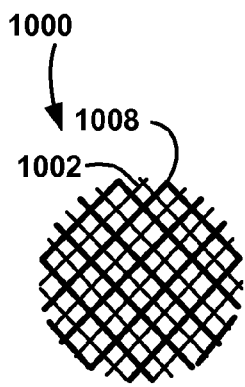
FIG. 10E
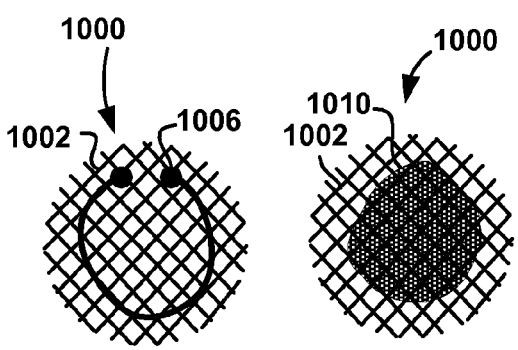
FIG. 10F
FIG. 10G

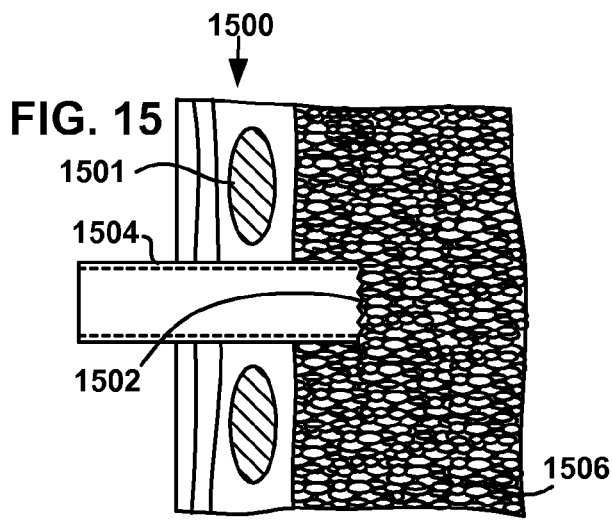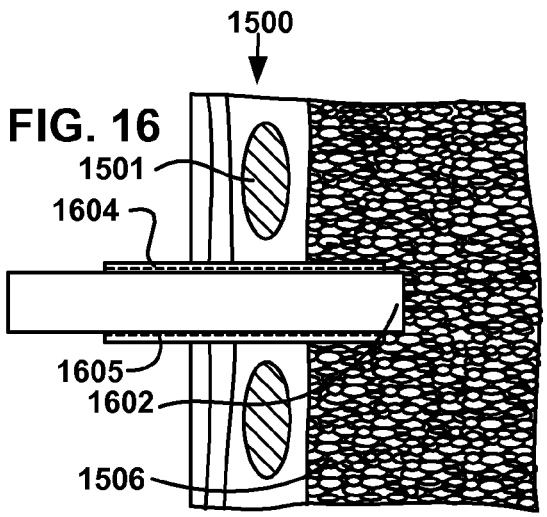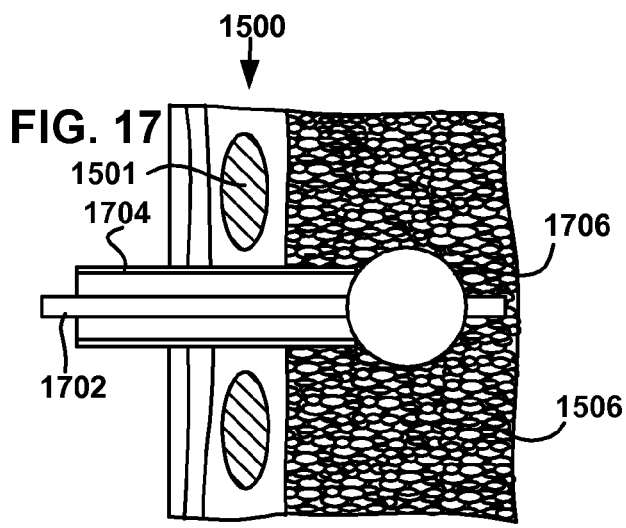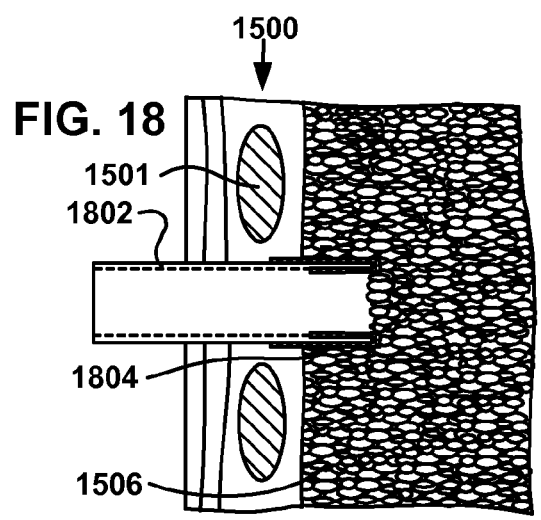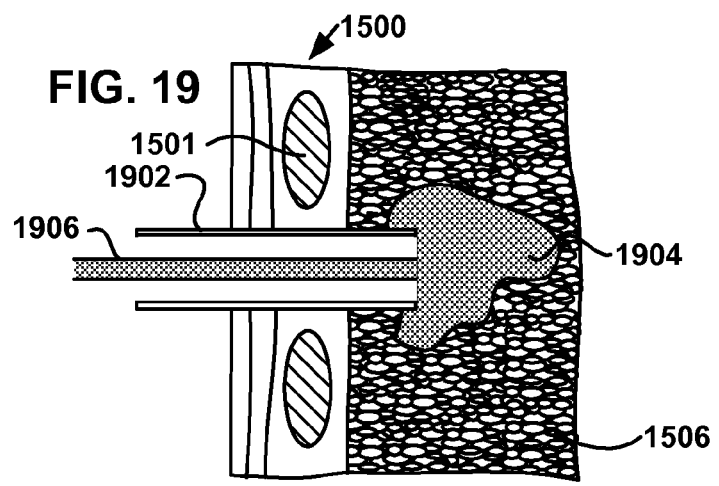

VARIABLE PARIETAL/VISCERAL PLEURAL COUPLING

FIELD OF THE INVENTION

The present invention relates to a device for treating diseased lungs, and more particularly, to a coupling device that provides for pleurodesis free access to a diseased lung.

BACKGROUND OF THE INVENTION

Chronic obstructive pulmonary disease is a persistent obstruction of the airways caused by chronic bronchitis and pulmonary emphysema. In the United States alone, approximately fourteen million people suffer from some form of chronic obstructive pulmonary disease and it is in the top ten leading causes of death.

Air enters the mammalian body through the nostrils and flows into the nasal cavities. As the air passes through the nostrils and nasal cavities, it is filtered, moistened and raised or lowered to approximately body temperature. The back of the nasal cavities is continuous with the pharynx (throat region); therefore, air may reach the pharynx from the nasal cavities or from the mouth. Accordingly, if equipped, the mammal may breathe through its nose or mouth. Generally air from the mouth is not as filtered or temperature regulated as air from the nostrils. The air in the pharynx flows from an opening in the floor of the pharynx and into the larynx (voice box). The epiglottis automatically closes off the larynx during swallowing so that solids and/or liquids enter the esophagus rather than the lower air passageways or airways. From the larynx, the air passes into the trachea, which divides into two branches, referred to as the bronchi. The bronchi are connected to the lungs.

The lungs are large, paired, spongy, elastic organs, which are positioned in the thoracic cavity. The lungs are in contact with the walls of the thoracic cavity. In humans, the right lung comprises three lobes and the left lung comprises two lobes. Lungs are paired in all mammals, but the number of lobes or sections of lungs varies from mammal to mammal. Healthy lungs, as discussed below, have a tremendous surface area for gas/air exchange. Both the left and right lung is covered with a pleural membrane. Essentially, the pleural membrane around each lung forms a continuous sac that encloses the lung. A pleural membrane also forms a lining for the thoracic cavity. The space between the pleural membrane forming the lining of the thoracic cavity and the pleural membranes enclosing the lungs is referred to as the pleural cavity. The pleural cavity comprises a film of fluid that serves as a lubricant between the lungs and the chest wall.

In the lungs, the bronchi branch into a multiplicity of smaller vessels referred to as bronchioles. Typically, there are more than one million bronchioles in each lung. Each bronchiole ends in a cluster of extremely small air sacs referred to as alveoli. An extremely thin, single layer of epithelial cells lining each alveolus wall and an extremely thin, single layer of epithelial cells lining the capillary walls separate the air/gas in the alveolus from the blood. Oxygen molecules in higher concentration pass by simple diffusion through the two thin layers from the alveoli into the blood in the pulmonary capillaries. Simultaneously, carbon dioxide molecules in higher concentration pass by simple diffusion through the two thin layers from the blood in the pulmonary capillaries into the alveoli.

Breathing is a mechanical process involving inspiration and expiration. The thoracic cavity is normally a closed system and air cannot enter or leave the lungs except through the trachea. If the chest wall is somehow compromised and air/gas enters the pleural cavity, the lungs will typically collapse. When the volume of the thoracic cavity is increased by the contraction of the diaphragm, the volume of the lungs is also increased. As the volume of the lungs increase, the pressure of the air in the lungs falls slightly below the pressure of the air external to the body (ambient air pressure). Accordingly, as a result of this slight pressure differential, external or ambient air flows through the respiratory passageways described above and fills the lungs until the pressure equalizes. This process is inspiration. When the diaphragm is relaxed, the volume of the thoracic cavity decreases, which in turn decreases the volume of the lungs. As the volume of the lungs decrease, the pressure of the air in the lungs rises slightly above the pressure of the air external to the body. Accordingly, as a result of this slight pressure differential, the air in the alveoli is expelled through the respiratory passageways until the pressure equalizes. This process is expiration.

Chronic obstructive pulmonary disease is a persistent obstruction of the airways caused by chronic bronchitis and pulmonary emphysema. Chronic bronchitis and acute bronchitis share certain similar characteristics; however, they are distinct diseases. Both chronic and acute bronchitis involve inflammation and constriction of the bronchial tubes and the bronchioles; however, acute bronchitis is generally associated with a viral and/or bacterial infection and its duration is typically much shorter than chronic bronchitis.

In chronic bronchitis, the bronchial tubes secrete too much mucus as part of the body's defensive mechanisms to inhaled foreign substances. Mucus membranes comprising ciliated cells (hair like structures) line the trachea and bronchi. The ciliated cells or cilia continuously push or sweep the mucus secreted from the mucus membranes in a direction away from the lungs and into the pharynx, where it is periodically swallowed. This sweeping action of the cilia functions to keep foreign matter from reaching the lungs. Foreign matter that is not filtered by the nose and larynx, as described above, becomes trapped in the mucus and is propelled by the cilia into the pharynx. When too much mucus is secreted, the ciliated cells may become damaged, leading to a decrease in the efficiency of the cilia to sweep the bronchial tubes and trachea of the mucus containing the foreign matter. This in turn causes the bronchioles to become constricted and inflamed and the individual becomes short of breath. In addition, the individual will develop a chronic cough as a means of attempting to clear the airways of excess mucus.

Individuals who suffer from chronic bronchitis may develop pulmonary emphysema. Pulmonary emphysema may be caused by a number of factors, including chronic bronchitis, long term exposure to inhaled irritants, e.g. air pollution, which damage the cilia, enzyme deficiencies and other pathological conditions. Pulmonary emphysema is a disease in which the alveoli walls, which are normally fairly rigid structures, are destroyed. The destruction of the alveoli walls is irreversible. In pulmonary emphysema, the alveoli of the lungs lose their elasticity, and eventually the walls between adjacent alveoli are destroyed. Accordingly, as more and more alveoli walls are lost, the air exchange (oxygen and carbon dioxide) surface area of the lungs is reduced until air exchange becomes seriously impaired.

Mucus hyper-secretion and dynamic airway compression are mechanisms of airflow limitation in chronic obstructive pulmonary disease. Mucus hyper-secretion is described above with respect to bronchitis. Dynamic airway compression results from the loss of tethering forces exerted on the airway due to the reduction in lung tissue elasticity. In other words, the breakdown of lung tissue leads to the reduced ability of the lungs to recoil and the loss of radial support of the airways. Consequently, the loss of elastic recoil of the lung tissue contributes to the inability of individuals to exhale completely. The loss of radial support of the airways also allows a collapsing phenomenon to occur during the expiratory phase of breathing. This collapsing phenomenon also intensifies the inability for individuals to exhale completely. As the inability to exhale completely increases, residual volume in the lungs also increases. This then causes the lung to establish in a hyperinflated state. The individual develops dyspnea in which the individual can only take short shallow breaths. Essentially, air is not effectively expelled and stale air accumulates in the lungs. Once the stale air accumulates in the lungs, the individual is deprived of oxygen.

Another aspect of an emphysematous lung is that the communicating flow of air between neighboring air sacs is much more prevalent as compared to healthy lungs. This phenomenon is known as collateral ventilation. However, since air cannot be expelled from the native airways due to the loss of tissue elastic recoil and radial support of the airways (dynamic collapse during exhalation), the increase in collateral ventilation does not significantly assist an individual in breathing.

There is no cure for pulmonary emphysema, only various treatments, including exercise, drug therapy, such as bronchodilating agents, lung volume reduction surgery and long term oxygen therapy. Long term oxygen therapy is widely accepted as the standard treatment for hypoxia caused by chronic obstructive pulmonary disease. Typically, oxygen therapy is prescribed using a nasal cannula. There are disadvantages associated with using the nasal cannula. Transtracheal oxygen therapy has become a viable alternative to long term oxygen therapy. Transtracheal oxygen therapy delivers oxygen directly to the lungs using a catheter that is placed through and down the trachea. Bronchodilating drugs only work on a percentage of patients with chronic obstructive pulmonary disease and generally only provide short-term relief. Oxygen therapy is impractical for the reasons described above, and lung volume reduction surgery is an extremely traumatic procedure that involves removing part of the lung. The long term benefits of lung volume reduction surgery are not fully known.

Accordingly, there exists a need for removing trapped gases from a diseased lung or lungs.

SUMMARY OF THE INVENTION

The present invention overcomes the limitations in treating diseases associated with chronic obstructive pulmonary disorders, such as emphysema and chronic bronchitis, as briefly described above. A long term oxygen therapy system may be utilized to effectively treat hypoxia caused by chronic obstructive pulmonary disease. A collateral ventilation bypass trap system may be utilized to take advantage of the above-described collateral ventilation phenomenon to increase the expiratory flow from a diseased lung or lungs, thereby treating another aspect of chronic obstructive pulmonary disease. Various methods may be utilized to determine the location or locations of the diseased tissue, for example, computerized axial tomography or CAT scans, magnetic resonance imaging or MRI, positron emission tomograph or PET, and/or standard X-ray imaging. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allow the entrapped air to bypass the native airways and be expelled to a containment system outside of the body.

The present invention is directed to variable parietal/visceral pleural couplings that allow for an air tight seal between the parietal and visceral pleura without the need for a pleurodesis. Once the air tight seal is created, any of the treatment devices described herein may be implanted.

In accordance with one aspect, the present invention is directed to a pleural coupling comprising at least one moveable member having a first section connected to the visceral pleura and a second section connected to the parietal pleura for establishing a pleurodesis free connection to allow trapped gases to flow from the lungs.

In order for the system to be effective, the components of the system are preferably sealed to the lung. Accordingly, methods and devices to create a chemically and/or mechanically localized pleurodesis of the present invention may be utilized to provide the seals required for effective sealing of the components of the long term oxygen therapy system and the collateral ventilation bypass trap system as well as other devices requiring pleurodesis.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 10A-10G are diagrammatic representations of an exemplary mechanical device for producing a chronic local adhesion in accordance with the present invention.

FIG. 15 is a diagrammatic representation of an exemplary modified tip of an implantable medical device in accordance with the present invention.

FIG. 16 is a diagrammatic representation of a first exemplary mechanical cleaning device in accordance with the present invention.

FIG. 17 is a diagrammatic representation of a second exemplary mechanical clearing device in accordance with the present invention.

FIG. 18 is a diagrammatic representation of a first chemical clearing device in accordance with the present invention.

FIG. 19 is a diagrammatic representation of a second chemical clearing device in accordance with the present invention.

DETAILED DESCRIPTION OF THE PREFERRED EMBODIMENTS

Long-Term Oxygen Therapy System

A long term oxygen therapy system and method may be utilized to deliver oxygen directly into the lung tissue in order to optimize oxygen transfer efficiency in the lungs. In other words, improved efficiency may be achieved if oxygen were to be delivered directly into the alveolar tissue in the lungs. In emphysema, alveoli walls are destroyed, thereby causing a decrease in air exchange surface area. As more alveoli walls are destroyed, collateral ventilation resistance is lowered. Accordingly, if it can be determined where collateral ventilation is occurring, then the diseased lung tissue may be isolated and the oxygen delivered to this precise location or locations. Various methods may be utilized to determine the diseased tissue locations, for example, computerized axial tomography or CAT scans, magnetic resonance imaging or MRI, positron emission tomograph or PET, and/or standard X-ray imaging. Once the diseased tissue is located, pressurized oxygen may be directly delivered to these diseased areas and more effectively and efficiently forced into the lung tissue for air exchange.

Once the location or locations of the diseased tissue are located, anastomotic openings are made in the thoracic cavity and lung or lungs and one or more oxygen carrying conduits are positioned and sealed therein. The one or more oxygen carrying conduits are connected to an oxygen source which supplies oxygen under elevated pressure directly to the diseased portion or portions of the lung or lungs. The pressurized oxygen essentially displaces the accumulated air and is thus more easily absorbed by the alveoli tissue. In addition, the long term oxygen therapy system may be configured in such a way as to provide collateral ventilation bypass in addition to direct oxygen therapy. In this configuration, an additional conduit may be connected between the main conduit and the individual's trachea with the appropriate valve arrangement. In this configuration, stale air may be removed through the trachea when the individual exhales since the trachea is directly linked with the diseased site or sites in the lung via the conduits. The long term oxygen therapy system improves oxygen transfer efficiency in the lungs thereby reducing oxygen supply requirements, which in turn reduces the patient's medical costs. The system also allows for improved self-image, improved mobility, and greater exercise capability and is easily maintained.

Figure 1:
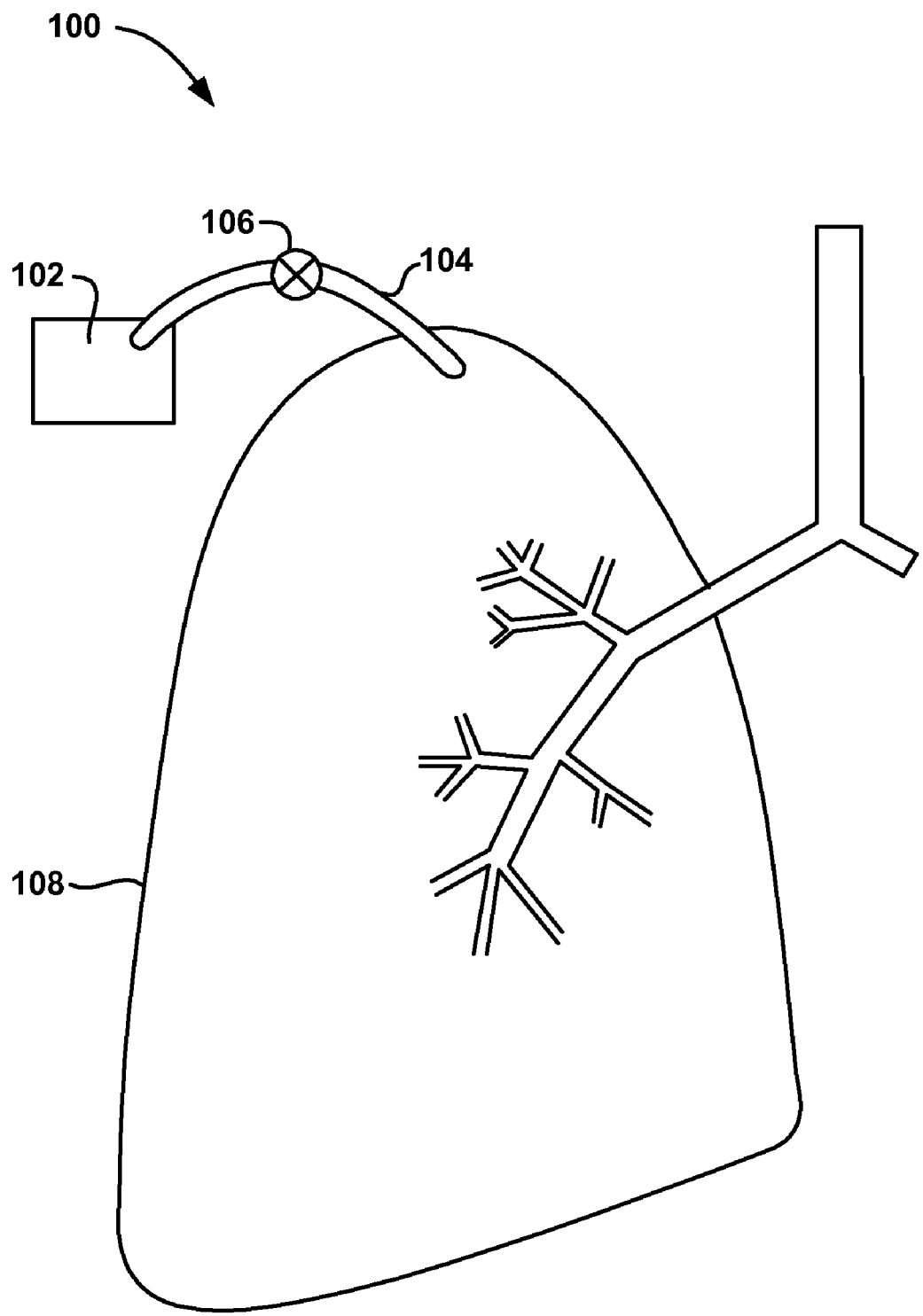
FIG. 1 is a diagrammatic representation of a first exemplary embodiment of the long term oxygen therapy system in accordance with the present invention.

FIG. 1 illustrates a first exemplary long term oxygen therapy system 100. The system 100 comprises an oxygen source 102, an oxygen carrying conduit 104 and a one-way valve 106. The oxygen source 102 may comprise any suitable device for supplying filtered oxygen under adjustably regulated pressures and flow rates, including pressurized oxygen tanks, liquid oxygen reservoirs, oxygen concentrators and the associated devices for controlling pressure and flow rate e.g. regulators. The oxygen carrying conduit 104 may comprise any suitable biocompatible tubing having a high resistance to damage caused by continuous oxygen exposure. The oxygen carrying conduit 104 comprises tubing having an inside diameter in the range from about 1/16 inch to about 1/2 inch and more preferably from about 1/8 inch to about 1/4 inch. The one-way valve 106 may comprise any suitable, in-line mechanical valve which allows oxygen to flow into the lungs 108 through the oxygen carrying conduit 104, but not from the lungs 108 back into the oxygen source 102. For example, a simple check valve may be utilized. As illustrated in FIG. 1, the oxygen carrying conduit 104 passes through the lung 108 at the site determined to have the highest degree of collateral ventilation.

The exemplary system 100 described above may be modified in a number of ways, including the use of an in-line filter. In this exemplary embodiment, both oxygen and air may flow through the system. In other words, during inhalation, oxygen is delivered to the lungs through the oxygen carrying conduit 104 and during exhalation, air from the lungs flow through the oxygen carrying conduit 104. The in-line filter would trap mucus and other contaminants, thereby preventing a blockage in the oxygen source 102. In this exemplary embodiment, no valve 106 would be utilized. The flow of oxygen into the lungs and the flow of air from the lungs is based on pressure differentials.

In order for the exemplary long term oxygen therapy system 100 to function, an air-tight seal is preferably maintained where the oxygen carrying conduit 104 passes through the thoracic cavity and lung. This seal is maintained in order to sustain the inflation/functionality of the lungs. If the seal is breached, air can enter the cavity and cause the lungs to collapse as described above.

A method to create this seal comprises forming adhesions between the visceral pleura of the lung and the inner wall of the thoracic cavity. This may be achieved using either chemical methods, including irritants such as Doxycycline and/or Bleomycin, surgical methods, including pleurectomy or horoscope talc pleurodesis, or radiotherapy methods, including radioactive gold or external radiation. All of these methods are known in the relevant art for creating pleurodesis. With a seal created at the site for the ventilation bypass, an intervention may be safely performed without the danger of creating a pneumothorax of the lung.

Figure 2:
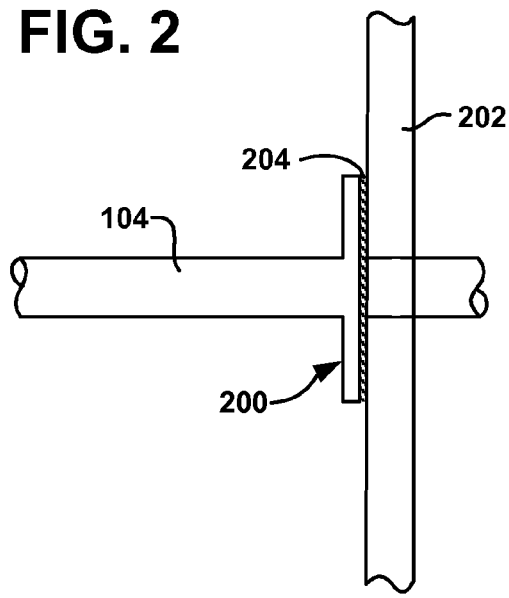
FIG. 2 is a diagrammatic representation of a first exemplary embodiment of a sealing device utilized in conjunction with the long term oxygen therapy system of the present invention.

Similarly to ostomy pouches or bags, the oxygen carrying conduit 104 may be sealed to the skin at the site of the ventilation bypass. In one exemplary embodiment, illustrated in FIG. 2, the oxygen carrying conduit 104 may be sealed to the skin of the thoracic wall 202 utilizing an adhesive 204. As illustrated, the oxygen carrying conduit 104 comprises a flange 200 having a biocompatible adhesive coating 204 on the skin contacting surface. The biocompatible adhesive 204 would provide a fluid tight seal between the flange 200 and the skin or epidermis of the thoracic wall 202. In a preferred embodiment, the biocompatible adhesive 204 provides a temporary fluid tight seal such that the oxygen carrying conduit 104 may be disconnected from the ventilation bypass site. This would allow for the site to be cleaned and for the long term oxygen therapy system 100 to undergo periodic maintenance.

Figure 3:
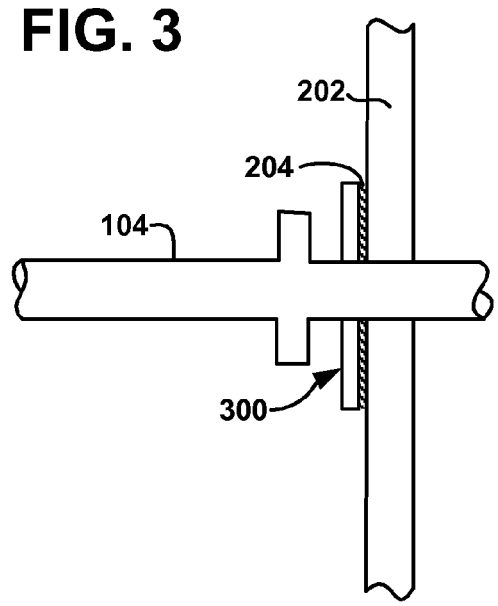
FIG. 3 is a diagrammatic representation of a second exemplary embodiment of a sealing device utilized in conjunction with the long term oxygen therapy system of the present invention.

FIG. 3 illustrates another exemplary embodiment for sealing the oxygen carrying conduit 104 to the skin of the thoracic wall 202 at the site of the ventilation bypass. In this exemplary embodiment, a coupling plate 300 is sealed to the skin at the site of the ventilation bypass by a biocompatible adhesive coating 204 or any other suitable means. The oxygen carrying conduit 104 is then connected to the coupling plate 300 by any suitable means, including threaded couplings and locking rings. The exemplary embodiment also allows for clearing of the site and maintenance of the system 100.

Figure 4:
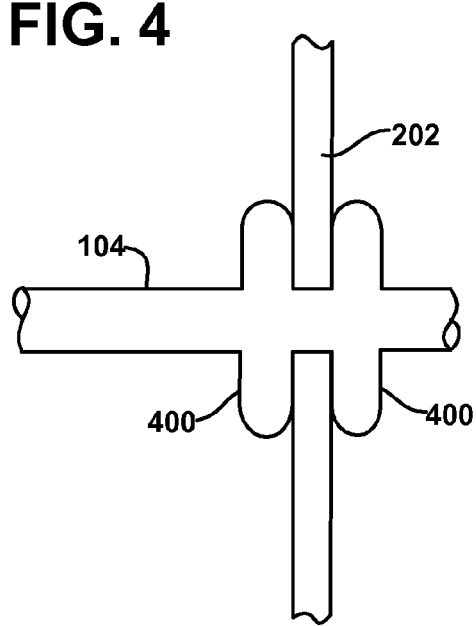
FIG. 4 is a diagrammatic representation of a third exemplary embodiment of a sealing device utilized in conjunction with the long term oxygen therapy system of the present invention.

FIG. 4 illustrates yet another exemplary embodiment for sealing the oxygen carrying conduit 104 to the skin of the thoracic wall 202 at the site of the ventilation bypass. In this exemplary embodiment, balloon flanges 400 may be utilized to create the seal. The balloon flanges 400 may be attached to the oxygen carrying conduit 104 such that in the deflated state, the oxygen carrying conduit 104 and one of the balloon flanges passes through the ventilation bypass anastomosis. The balloon flanges 400 are spaced apart a sufficient distance such that the balloon flanges remain on opposite sides of the thoracic wall 202. When inflated, the balloons expand and form a fluid tight seal by sandwiching the thoracic wall. Once again, this exemplary embodiment allows for easy removal of the oxygen carrying conduit 104.

Figure 5:
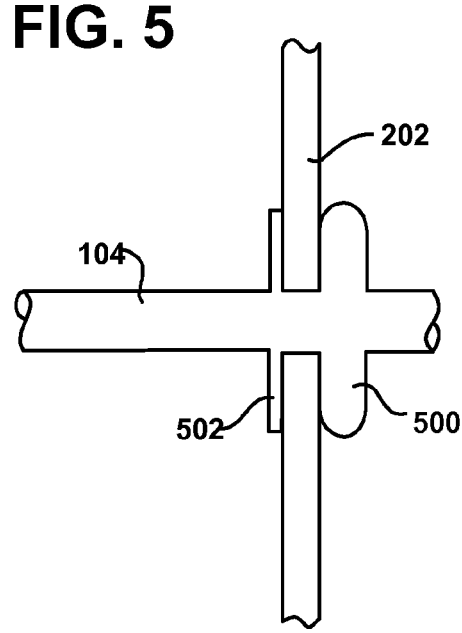
FIG. 5 is a diagrammatic representation of a fourth exemplary embodiment of a sealing device utilized in conjunction with the long term oxygen therapy system of the present invention.

FIG. 5 illustrates yet another exemplary embodiment for sealing the oxygen carrying conduit 104 to the skin of the thoracic wall 202 at the site of the ventilation bypass. In this exemplary embodiment, a single balloon flange 500 is utilized in combination with a fixed flange 502. The balloon flange 500 is connected to the oxygen carrying conduit 104 in the same manner as described above. In this exemplary embodiment, the balloon flange 500, when inflated, forms the fluid tight seal. The fixed flange 502, which is maintained against the skin of the thoracic wall 202, provides the structural support against which the balloon exerts pressure to form the seal.

Collateral Ventilation Bypass System

The above-described long term oxygen therapy system may be utilized to effectively treat hypoxia caused by chronic obstructive pulmonary disease; however, other means may be desirable to treat other aspects of the disease. A collateral ventilation bypass trap system utilizes the above-described collateral ventilation phenomenon to increase the expiratory flow from a diseased lung or lungs, thereby treating another aspect of chronic obstructive pulmonary disease. Essentially, the most collaterally ventilated area of the lung or lungs is determined utilizing the scanning techniques described above. Once this area or areas are located, a conduit or conduits are positioned in a passage or passages that access the outer pleural layer of the diseased lung or lungs. The conduit or conduits utilize the collateral ventilation of the lung or lungs and allows the entrapped air to bypass the native airways and be expelled to a containment system outside of the body.

Figure 6:
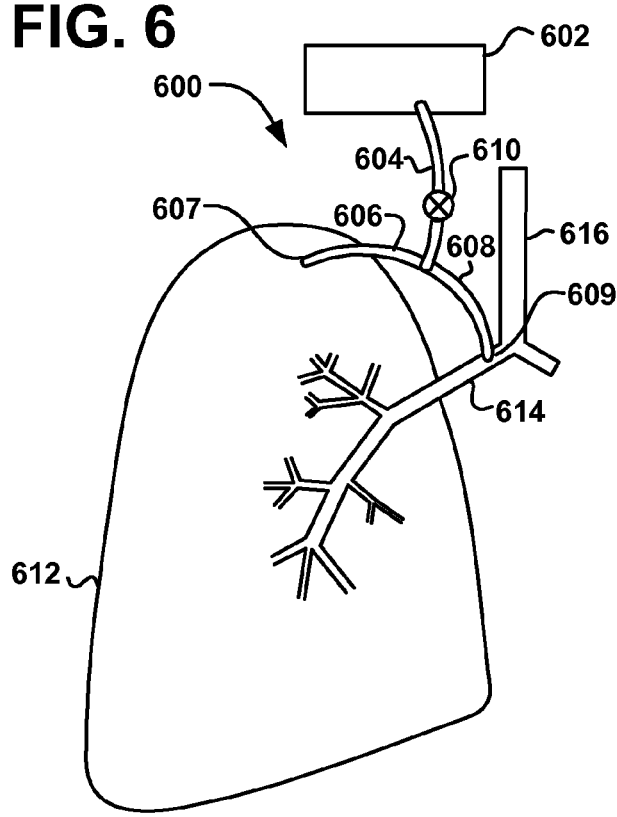
FIG. 6 is a diagrammatic representation of a second exemplary embodiment of the long term oxygen therapy system in accordance with the present invention.

If an individual has difficulty exhaling and requires additional oxygen, collateral ventilation bypass may be combined with direct oxygen therapy. FIG. 6 illustrates an exemplary embodiment of a collateral ventilation bypass/direct oxygen therapy system 600. The system 600 comprises an oxygen source 602 (with potential filter), an oxygen carrying conduit 604 having two branches 606 and 608, and a control valve 610. The oxygen source 602 and oxygen carrying conduit 604 may comprise components similar to the above-described exemplary embodiment illustrated in FIG. 1.

In this exemplary embodiment, as shown in FIG. 6, when the individual inhales, the valve 610 is open and oxygen flows into the lung 612 and into the bronchial tube 614. In an alternate exemplary embodiment, the branch 608 may be connected to the trachea 616. Accordingly, during inhalation oxygen flows to the diseased site in the lung or lungs and to other parts of the lung through the normal bronchial passages. During exhalation, the valve 610 is closed so that no oxygen is delivered and air in the diseased portion of the lung may flow from the lung 612, through one branch 606 and into the second branch 608 and finally into the bronchial tube 614. In this manner, stale air is removed and oxygen is directly delivered. Once again, as described above, the flow of oxygen and air is regulated by simple pressure differentials. A sealed joint 607 is provided at the end of branch 606, and a sealed joint 609 is provided at the end of branch 608. The connection and sealing of the oxygen carrying conduit 604 and branches 606, 608 to the lung 612 and bronchial tube 614 may be made in a manner similar to that described above.

Figure 7:
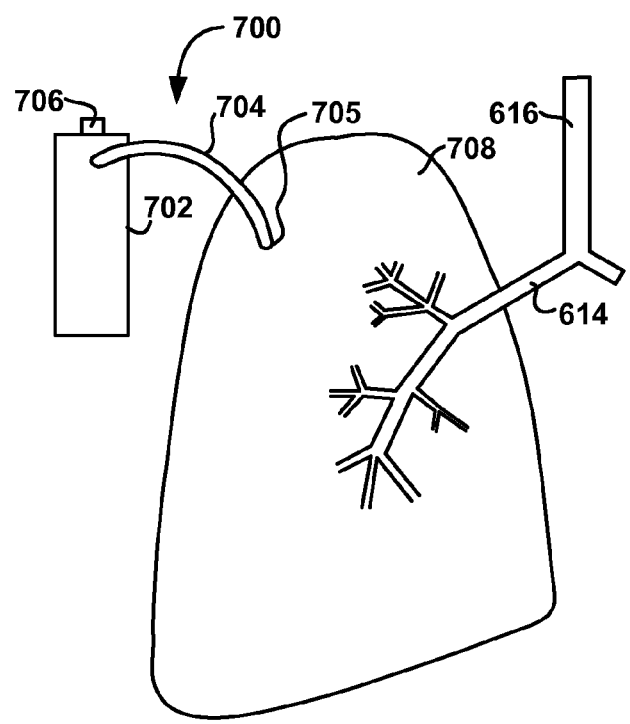
FIG. 7 is a diagrammatic representation of a first exemplary embodiment of a collateral ventilation bypass trap system in accordance with the present invention.

FIG. 7 illustrates a first exemplary collateral ventilation bypass trap system 700. The system 700 comprises a trap 702, an air carrying conduit 704 and a filter/one-way valve 706. The air carrying conduit 704 creates a fluid communication between an individual's lung 708 and the trap 702 through the filter/one-way valve 706. It is important to note that although a single conduit 704 is illustrated, multiple conduits may be utilized in each lung 708 if it is determined that there are more than one area of high collateral ventilation.

The trap 702 may comprise any suitable device for collecting discharge from the individual's lung or lungs 708. Essentially, the trap 702 is simply a containment vessel for temporarily storing discharge from the lungs, for example, mucous and other fluids that may accumulate in the lungs. The trap 702 may comprise any suitable shape and may be formed from any suitable metallic or non-metallic materials. Preferably, the trap 702 should be formed from a lightweight, non-corrosive material. In addition, the trap 702 should be designed in such a manner as to allow for effective and efficient cleaning. In one exemplary embodiment, the trap 702 may comprise disposable liners that may be removed when the trap 702 is full. The trap 702 may be formed from a transparent material or comprise an indicator window so that it may be easily determined when the trap 702 should be emptied or cleaned. A lightweight trap 702 increases the patient's mobility.

The filter/one-way valve 706 may be attached to the trap 702 by any suitable means, including threaded fittings or compression type fittings commonly utilized in compressor connections. The filter/one-way valve 706 serves a number of functions. The filter/one-way valve 706 allows the air from the individual's lung or lungs 708 to exit the trap 702 while maintaining the fluid discharge and solid particulate matter in the trap 702. This filter/one-way valve 706 would essentially maintain the pressure in the trap 702 below that of the pressure inside the individual's lung or lungs 708 so that the flow of air from the lungs 708 to the trap 702 is maintained in this one direction. The filter portion of the filter/one-way valve 706 may be designed to capture particulate matter of a particular size which is suspended in the air, but allows the clean air to pass therethrough and be vented to the ambient environment. The filter portion may also be designed in such a manner as to reduce the moisture content of the exhaled air.

The air carrying conduit 704 connects the trap 702 to the lung or lungs 708 of the patient through the filter/one-way valve 706. The air carrying conduit 704 may comprise any suitable biocompatible tubing having a resistance to the gases contained in air. The air carrying conduit 704 comprises tubing having an inside diameter in the range from about 1/16 inch to about 1/2 inch, and more preferably from about 1/8 inch to about 1/4 inch. The filter/one-way valve 706 may comprise any suitable valve which allows air to flow from the lung or lungs 708 through the air carrying conduit 704, but not from the trap 702 back to the lungs 708. For example, a simple check valve may be utilized. The air carrying conduit 704 may be connected to the filter/one-way valve 706 by any suitable means. Preferably, a quick release mechanism is utilized so that the trap may be easily removed for maintenance.

As illustrated in FIG. 7, the air carrying conduit 704 passes through the lung 708 at the site determined to have the highest degree of collateral ventilation. If more than one site is determined, multiple air carrying conduits 704 may be utilized. The connection of multiple air carrying conduits 704 to the filter/one-way valve 706 may be accomplished by any suitable means, including an octopus device similar to that utilized in scuba diving regulators.

The air carrying conduit 704 is preferably able to withstand and resist collapsing once in place. Since air will travel through the conduit 704, if the conduit is crushed and unable to recover, the effectiveness of the system is diminished. Accordingly, a crush recoverable material may be incorporated into the air carrying conduit 704 in order to make it crush recoverable. Any number of suitable materials may be utilized. For example, Nitinol incorporated into the conduit 704 will give the conduit collapse resistance and collapse recovery properties.

Expandable features at the end of the conduit 704 may be used to aid in maintaining contact and sealing the conduit 704 to the lung pleura. Nitinol incorporated into the conduit 704 will provide the ability to deliver the conduit 704 in a compressed state and then deployed in an expanded state to secure it in place. Shoulders at the end of the conduit may also provide a mechanical stop for insertion and an area for an adhesive/sealant to join as described in detail subsequently.

In order for the exemplary collateral ventilation bypass trap system 700 to function, an air-tight seal is preferably maintained where the air carrying conduit 704 passes through the thoracic cavity and lungs 708. A sealed joint 705 is provided at the end of conduit 704. This seal is maintained in order to sustain the inflation/functionality of the lungs. If the seal is breached, air can enter the cavity and cause the lungs to collapse. One exemplary method for creating the seal comprises forming adhesions between the visceral pleura of the lung and the inner wall of the thoracic cavity. This may be achieved using either chemical methods, including irritants such as Doxycycline and/or Bleomycin, surgical methods, including pleurectomy or thorascopic talc pleurodesis, or radiotherapy methods, including radioactive gold or external radiation. All of these methods are known in the relevant art for creating pleurodesis. In another alternate exemplary embodiment, a sealed joint between the air carrying conduit 704 and the outer pleural layer includes using various glues to help with the adhesion/sealing of the air carrying conduit 704. Currently, Focal Inc. markets a sealant available under the trade name FOCAL/SEAL-L which is indicated for use on a lung for sealing purposes. Focal/Seal-L is activated by light in order to cure the sealant. Another seal available under the trade name THOREX, which is manufactured by Surgical Sealants Inc., is currently conducting a clinical trial for lung sealing indications. Thorex is a two-part sealant that has a set curing time after the two parts are mixed.

The creation of the opening in the chest cavity may be accomplished in a number of ways. For example, the procedure may be accomplished using an open chest procedure, sternotomy or thoracotomy. Alternately, the procedure may be accomplished using a laparoscopic technique, which is less invasive. Regardless of the procedure utilized, the seal should be established while the lung is at least partially inflated in order to maintain a solid adhesive surface. The opening may then be made after the joint has been adequately created between the conduit component and the lung pleural surface. The opening should be adequate in cross-sectional area in order to provide sufficient decompression of the hyperinflated lung. This opening, as stated above, may be created using a number of different techniques such as cutting, piercing, dilating, blunt dissection, radio frequency energy, ultrasonic energy, microwave energy, or cryoblative energy.

The air carrying conduit 704 may be sealed to the skin at the site by any of the means and methods described above with respect to the oxygen carrying conduit 704 and illustrated in FIGS. 2 through 5.

In operation, when an individual exhales, the pressure in the lungs is greater than the pressure in the trap 702. Accordingly, the air in the highly collateralized areas of the lung will travel through the air carrying conduit 704 to the trap 702. This operation will allow the individual to more easily and completely exhale.

Localized Pleurodesis Systems and Method

In the above-described exemplary apparatus and procedure for increasing expiratory flow from a diseased lung using the phenomenon of collateral ventilation, there will be an optimal location to penetrate the outer pleura of the lung to access the most collaterally ventilated area or areas of the lung. As described above, there are a variety of techniques to locate the most collaterally ventilated area or areas of the lungs. Since a device or component of the apparatus functions to allow the air entrapped in the lung to bypass the native airways and be expelled outside of the body, it is particularly advantageous to provide an air-tight seal of the parietal (thoracic wall) and visceral (lung) pleurae. If a proper air-tight seal is not created between the device, parietal and visceral pleurae, then a pneumothorax (collapsed lung) may occur. Essentially, in any circumstance where the lung is punctured and a device inserted, an air-tight seal should preferably be maintained.

One way to achieve an air-tight seal is through pleurodesis, i.e. an obliteration of the pleural space. There are a number of pleurodesis methods, including chemical, surgical and radiological. In chemical pleurodesis, an agent such as tetracycline, doxycycline, bleomycin or nitrogen mustard may be utilized. In surgical pleurodesis, a pleurectomy or a thorascopic talc procedure may be performed. In radiological procedures, radioactive gold or external radiation may be utilized. In the present invention, chemical pleurodesis is utilized. Exemplary methods for creating the seal comprises forming adhesions between the visceral pleura of the lung and the inner wall of the thoracic cavity using chemical methods, including irritants such as Doxycycline and/or Bleomycin, surgical methods, including pleurectomy or thorascopic talc pleurodesis. In another alternate exemplary embodiment, a sealed joint between the air carrying conduit 704 and the outer pleural layer includes using various glues to help with the adhesion/sealing of the air carrying conduit 704. Currently, Focal Inc. markets a sealant available under the trade name FOCAL/SEAL-L which is indicated for use on a lung for sealing purposes. Focal/Seal-L is activated by light in order to cure the sealant. Another seal available under the trade name THOREX, which is manufactured by Surgical Sealants Inc., is currently conducting a clinical trial for lung sealing indications. Thorex is a two-part sealant that has a set curing time after the two parts are mixed.

Exemplary devices and methods for delivering a chemical(s) or agent(s) in a localized manner for ensuring a proper air-tight seal of the above-described apparatus is described below. The chemical(s), agent(s) and/or compound(s) are used to create a pleurodesis between the parietal and visceral pleura so that a component of the apparatus may penetrate through the particular area and not result in a pneumothorax. There are a number of chemical(s), agent(s) and/or compound(s) that may be utilized to create a pleurodesis in the pleural space. The chemical(s), agent(s) and/or compound(s) include talc, tetracycline, doxycycline, bleomycin and minocycline.

Figure 8:
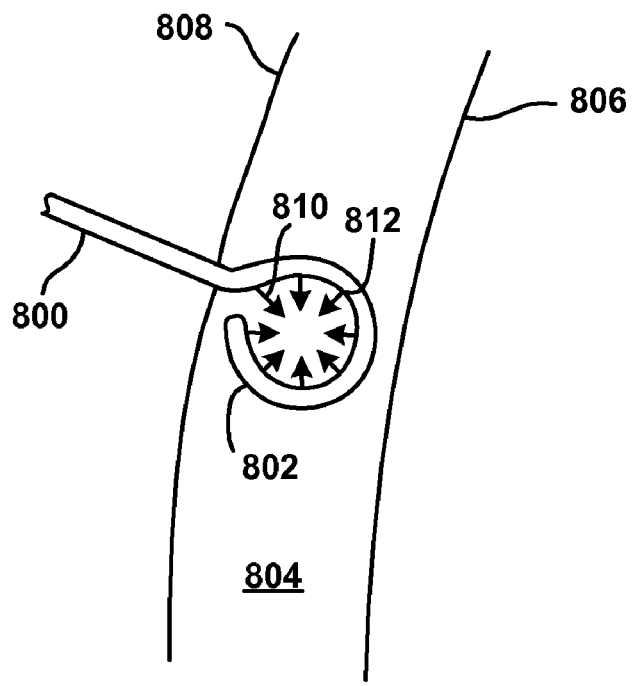
FIG. 8 is a diagrammatic representation of a first exemplary embodiment of a localized pleurodesis chemical delivery system.

In one exemplary embodiment, a modified drug delivery catheter may be utilized to deliver chemical(s), agent(s) and/or compound(s) to a localized area for creating a pleurodesis in that area. In this exemplary embodiment, the pleurodesis is formed and then the conduit 704, as illustrated in FIG. 7, is positioned in the lung 708 through the area of the pleurodesis. The drug delivery catheter provides a minimally invasive means for creating a localized pleurodesis. Referring to FIG. 8, there is illustrated an exemplary embodiment of a drug delivery catheter that may be utilized in accordance with the present invention. Any number of drug delivery catheters may be utilized. In addition, the distal tip of the catheter may comprise any suitable size, shape or configuration thereby enabling the formation of a pleurodesis having any size, shape or configuration.

As illustrated in FIG. 8, the catheter 800 is inserted into the patient such that the distal end 802 is positioned in the pleural space 804 between the thoracic wall 808 and the lung 806. In the illustrated exemplary embodiment, the distal end 802 of the catheter 800 comprises a substantially circular shape that would allow the chemical(s), agent(s) and/or compound(s) to be released towards the inner diameter of the substantially circular shape as indicated by arrows 810. The distal end 802 of the catheter 800 comprising a plurality of holes or openings 812 through which the chemical(s), agent(s) and/or compound(s) are released. As stated above, the distal end 802 may comprise any suitable size, shape or configuration. Once the chemical(s), agent(s) and/or compound(s) are delivered, the catheter 800 may be removed to allow for implantation of the conduit 704 (FIG. 7). Alternately, the catheter 800 may be utilized to facilitate delivery of the conduit 704.

The distal end or tip 802 of the catheter 800 should preferably maintain its desired size, shape and/or configuration once deployed in the pleural space. This may be accomplished in a number of ways. For example, the material forming the distal end 802 of the catheter 800 may be selected such that it has a certain degree of flexibility for insertion of the catheter 800 and a certain degree of shape memory such that it resumes its original or programmed shape once deployed. Any number of biocompatible polymers with these properties may be utilized. In an alternate embodiment, another material may be utilized. For example, a metallic material having shape memory characteristics may be integrated into the distal end 802 of the catheter 800. This metallic material may include Nitinol or stainless steel. In addition, the metallic material may be radiopaque or comprise radiopaque markers. By having a radiopaque material or radiopaque markers, the catheter 800 may be viewed under x-ray fluoroscopy and aid in determining when the catheter 800 is at the location of the highest collateral ventilation.

In another alternate exemplary embodiment, a local drug delivery device may be utilized to deliver the pleurodesis chemical(s), agent(s) and/or compound(s). In this exemplary embodiment, the pleurodesis is formed and then the conduit 704, as illustrated in FIG. 7, is positioned in the lung 708 through the pleurodesis. In this exemplary embodiment, chemical(s), agent(s) and/or compound(s) may be affixed to an implantable medical device. The medical device is then implanted in the pleural cavity at a particular site and the chemical(s), agent(s) and/or compound(s) are released therefrom to form or create the pleurodesis.

Any of the above-described chemical(s), agent(s) and/or compound(s) may be affixed to the medical device. The chemical(s), agent(s) and/or compound(s) may be affixed to the medical device in any suitable manner. For example, the chemical(s), agent(s) and/or compound(s) may be coated on the device utilizing any number of well known techniques including, spin coating, spraying or dipping, they may be incorporated into a polymeric matrix that is affixed to the surface of the medical device, they may be impregnated into the outer surface of the medical device, they may be incorporated into holes or chambers in the medical device, they may be coated onto the surface of the medical device and then coated with a polymeric layer that acts as a diffusion barrier for controlled release of the chemical(s), agent(s) and/or compound(s), they may be incorporated directly into the material forming the medical device, or any combination of the above-described techniques. In another alternate embodiment, the medical device may be formed from a biodegradable material which elutes the chemical(s), agent(s) and/or compound(s) as the device degrades.

Figure 9:
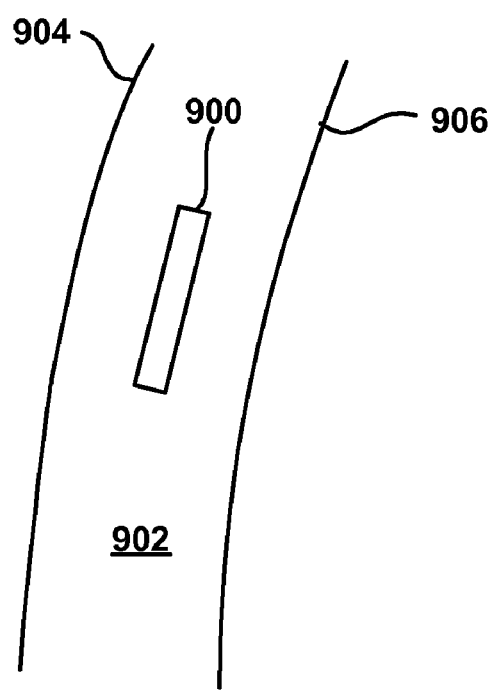
FIG. 9 is a diagrammatic representation of a second exemplary embodiment of a localized pleurodesis chemical delivery system.

The implantable medical device may comprise any suitable size, shape and/or configuration, and may be formed using any suitable biocompatible material. FIG. 9 illustrates one exemplary embodiment of an implantable medical device 900. In this embodiment, the implantable medical device 900 comprises a substantially cylindrical disk 900. The disk 900 is positioned in the pleural space 902 between the thoracic wall 904 and the lung 906. Once in position, the disk 900 elutes or otherwise releases the chemical(s), agent(s) and/or compound(s) that form the pleurodesis. The release rate may be precisely controlled by using any of the various techniques described above, for example, a polymeric diffusion barrier. Also, as stated above, the disk 900 may be formed from a biodegradable material that elutes the chemical(s), agent(s) and/or compound(s) as the disk 900 itself disintegrates or dissolves. Depending upon the material utilized in the construction of the disk 900, a non-biodegradable disk 900 may or may not require removal from the pleural cavity 902 once the pleurodesis is formed. For example, it may be desirable that the disk 900 is a permanent implant that becomes integral with the pleurodesis.

As described in the previous exemplary embodiment, the disk 900 may comprise a radiopaque marker or be formed from a radiopaque material. The radiopaque marker or material allows the disk 900 to be seen under fluoroscopy and then positioned accurately.

In yet another alternate exemplary embodiment, the fluid characteristics of the chemical(s), agent(s) and/or compound(s) may be altered. For example, the chemical(s), agent(s) and/or compound(s) may be made more viscous. With a more viscous chemical agent and/or compound, there would be less chance of the chemical, agent and/or compound moving from the desired location in the pleural space. The chemical(s), agent(s) and/or compound(s) may also comprise radiopaque constituents. Making the chemical(s), agent(s) and/or compounds radiopaque would allow the confirmation of the location of the chemical(s), agent(s) and/or compound(s) with regard to the optimal location of collateral ventilation. The chemical(s), agent(s) and/or compound(s) as modified above may be utilized in conjunction with standard chemical pleurodesis devices and processes or in conjunction with the exemplary embodiments set forth above.

In an alternate exemplary embodiment, an implantable structure in combination with a chemical agent and/or a therapeutic agent may be utilized to create a localized area where the visceral and parietal pleura of the lung are fused together. In this exemplary embodiment, a localized pleurodesis may be created utilizing either or both a mechanical component and a chemical component. The purpose of the chemical component is to provide an acute adhesion between the parietal and visceral pleura, while the mechanical component is utilized to provide a chronic adhesion. In other words, the acute adhesion provided by the chemical adhesive would provide enough stability at the implant location on the lung to allow for the mechanical component to create a chronic adhesion. The combination of a chemical adhesive with a tissue growth promoting material in a specific area of the lung would promote a well-controlled localized pleurodesis reaction.

FIGS. 10A, 10B and 10C illustrate a first exemplary mechanical device 1000 for providing a chronic adhesion. FIG. 10A shows a close up view of the sectional view of mechanical device 1000 shown in FIG. 10B. FIG. 10C shows a cutaway view of the mechanical device 1000 shown in FIG. 10B on the surface of lung 1022. As illustrated, the mechanical device 1000 comprises a mesh 1002 that may be formed out of any suitable biocompatible material. For example, the mesh 1002 may comprise a metallic material, a polymeric material and/or a ceramic material. Primary variations of this material may be bio-resorbable or non-resorbable materials that promote tissue growth. Any type of mesh may be utilized including hernia repair meshes, laparoscopic meshes and surgical meshes. The mesh 1002 may be inserted between the parietal 1005 and visceral 1007 pleura at the desired location by any suitable means as set forth below. The mesh 1002 may be simply positioned or secured in place by any number of suitable means. In a preferred exemplary embodiment, the mechanical device is secured in such a manner than ensures the apposition of the device to either and/or both the visceral pleura 1007 and parietal pleura 1005. As shown in FIG. 10G, this may be accomplished by a percutaneous application of a chemical adhesive 1010 after the lung is inflated to allow for a chemical agent to form an acute adhesion between the visceral pleura 1007 and parietal pleura 1005. The chemical adhesive 1010 may include fibrin backed adhesive, cyanoacrylate bond adhesive or aldehyde bond adhesive. Alternately, as shown in FIG. 10D, a suture 1004 may be threaded into the device and pulled along with the visceral pleura 1007 against the parietal pleura 1005 of the thoracic wall 1020.

Radiological markers may be incorporated into the device 1000 thereby increasing its radiopacity under fluoroscopy. Essentially, this would ensure that in follow-up examinations, the exact location of where the localized pleurodesis has grown would be easy to find. These markers may be incorporated into the device 1000 in any number of suitable ways. For example, as shown in FIG. 10F, a wire ring 1006 may be woven into the spot of the tissue growth promoting material of the mesh. Alternately, as shown in FIG. 10E, radiological fibers 1008 may be incorporated into the tissue promoting fibers of the mesh 1002. In yet another alternate exemplary embodiment, a radiological chemical adhesive may be utilized as shown in FIG. 10G.

The delivery of the device 1000 may be approached utilizing any number of acceptable procedures. In one exemplary embodiment, a thoracotomy procedure to open the thoracic cavity may be performed, and the device 1000 placed directly in the location. In another exemplary embodiment, a minimally invasive approach using a cannula or such like device may be utilized to percutaneously access the thoracic cavity. The device 1000 could then be entirely delivered via a delivery system through the cannula or sheath.

Current pleurodesis procedures look to create adhesion between the entire lung and the thoracic wall, effectively sealing off any thoracic cavity spaces. The device of the present invention allows for a small controlled local pleurodesis to form, thereby reducing potentially painful side effects and minimize pleural adhesions for subsequent thoracic interventions. Additionally, due to the dynamic nature between the lung and thoracic wall, it may be difficult to create a chronic local pleurodesis without the help of a clinical adhesive to provide acute stability to the location of intent.

Anastomosis Devices and Methods

For any of the above-described devices that require access to a patient's lung or lungs via surgically attaching a conduit to the lung or lungs and not through a native airway, the visceral pleura must be properly attached to the conduit in order to properly seal around the conduit. A technique that may be utilized is to gather and attach the visceral pleura around the conduit using a purse-string suture or similar technique. This technique, however, requires the handling of the pleura in order to provide a counterforce on the pleura as the conduit is being positioned in the lung. In addition, what makes this technique more difficult is as soon as an access is made through the pleura for the conduit, the lung will immediately leak air and collapse to a smaller size. Therefore, providing a counterforce to insert a conduit or other device described herein through the access in the lung becomes even more vital.

The visceral pleura of the lung are thin and somewhat fragile. Manipulation of the pleura using surgical instruments such as forceps or hemostats may create a break in the pleura. It is often difficult to seal the leak that will follow and the leak will typically result in a pneumothorax or a collapsed lung. In an emphysematous lung where the patient is already compromised with the inability to breath, a pneumothorax may potentially lead to serious complications, including death.

Although there are devices that resect lung tissue and help seal it thereafter, there are currently no devices that enter the lung through the visceral pleura. Lung resection and buttressing devices do not need to rely on stabilization and counterforce. Accordingly, the present invention is directed to a device that would provide the ability to insert a conduit or other device in the lung with a significantly decreased chance of injuring the lung if conventional surgical tools are utilized. Essentially, if a device could stabilize the visceral pleura and provide the counterforce without damaging the pleura, the procedure of inserting the device in the lung could become easier, faster and less conducive to injuring the pleura.

Figure 11A:
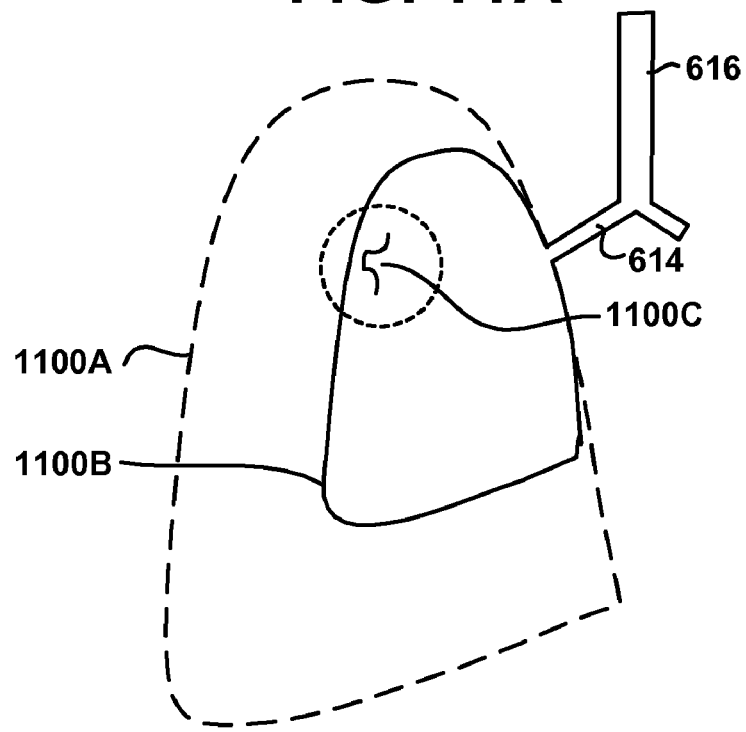
FIGS. 11A and 11B are diagrammatic representations of an exemplary pulmonary pleural stabilizer in accordance with the present invention.
Figure 11B:
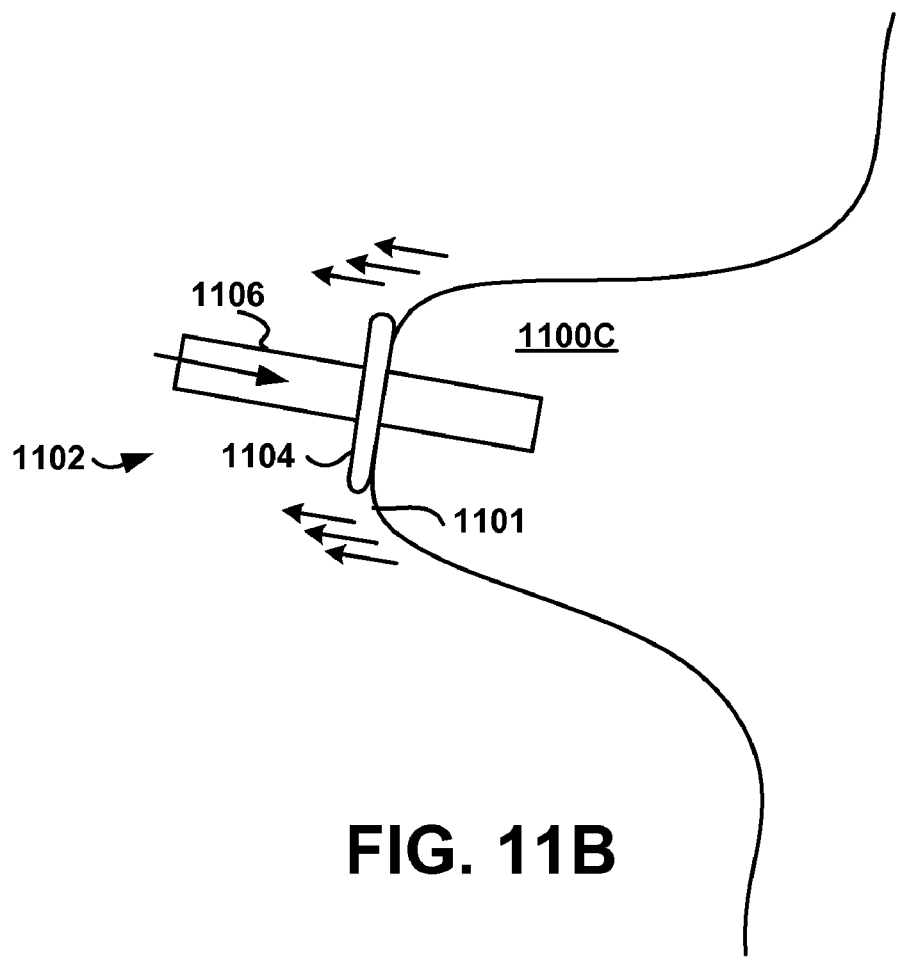
Figure 12A:
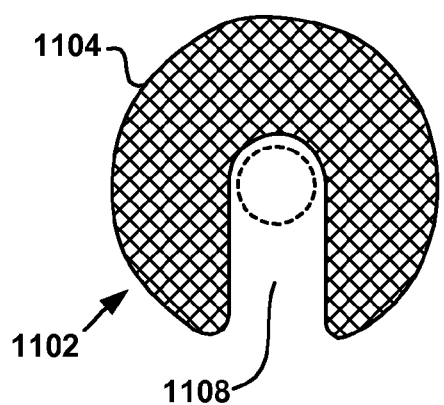
FIGS. 12A, 12B, 12C and 12D are diagrammatic representations of two exemplary holding devices in accordance with the present invention.
Figure 12B:
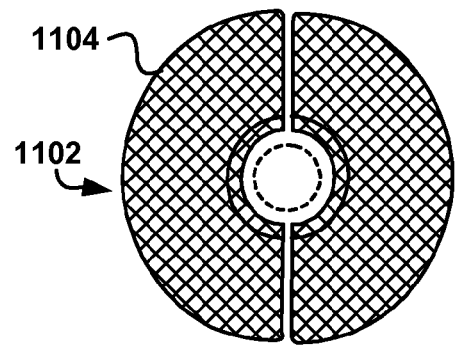
Figure 12C:
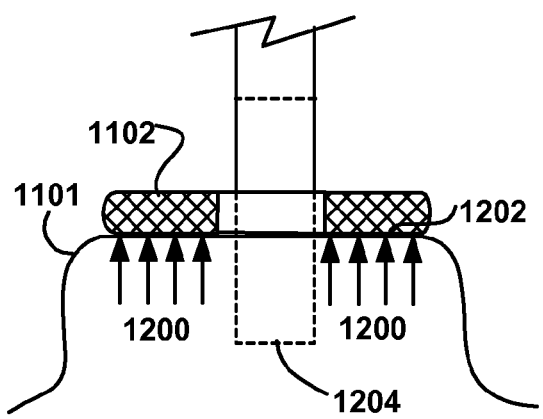
Figure 12D:
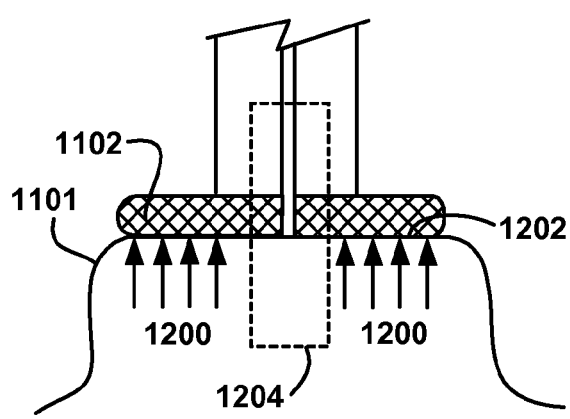

In accordance with one exemplary embodiment, a vacuum assist device 1102 may be utilized to hold the pleura while a conduit or other device is being positioned in the lung. Referring to FIG. 11A, there is illustrated an inflated lung 1100A and a deflated lung 1100B and an access point 1100C. Illustrated in FIG. 11B is a vacuum assist device 1102 which comprises a substantially disc-like structure or removable holding device 1104 illustrated in FIGS. 12A, 12B, 12C and 12D, that exerts a vacuum force 1200 on the visceral pleura 1101 in contact therewith and an insertion envelope 1106 through which a conduit or other device may be inserted. Although any shape device may be utilized, for ease of explanation a substantially disc like structure is illustrated.

As illustrated in FIGS. 11B, 12A, 12B, 12C and 12D the disc-like structure 1104 preferably has one substantially flat surface 1202 that makes contact with the visceral pleura 1101. This flat surface has one or more openings through which a vacuum force that is created by an external source (not illustrated) is transmitted to the visceral pleura. This gentle vacuum force, in the range from about 10 mm Hg to about 450 mm Hg is preferably evenly distributed over the substantially flat surface and gently pulls the visceral pleura 1101 into contact with the substantially flat surface 1202. In one exemplary embodiment, illustrated in FIG. 12A the disc like structure 1104 comprises a slit like opening 1108 that forms the envelope 1106. In an alternate exemplary embodiment, illustrated in FIG. 12b, the disc like structure 1104 comprises a two piece structure that when connected together forms the envelope 1106. The disc like structure 1104 may be formed from any suitable biocompatible material that will not damage the visceral pleura and is easily removed from the pleural space when the vacuum is cut off.

Once the vacuum assist device 1102 is inserted and placed into contact with the visceral pleura 1101, the vacuum is started and draws and holds the visceral pleura 1101 in place while the conduit 1204 or other device is inserted through the envelope 1106. The vacuum assist device 1102 maintains the counter-pressure for insertion and sealing without damaging the lung tissue. When the seal is created, the vacuum is cut off and the device 1102 is removed.

The vacuum pressure or negative pressure may be created in a variety of ways. For example, surgical sites are typically equipped with vacuum devices that may be regulated to draw a negative pressure in the desired range. A simple pressure regulator or vacuum regulator may be connected between two vacuum sources and the device 1102 by any suitable means. In alternate exemplary embodiments, the device 1102 may comprise a vacuum pump and regulator. The vacuum pump may use hospital power or be a self-contained battery power unit.

As described above, once a device such as a conduit 1204 is inserted into the lung, the device must be sealed to the lung tissue. Also as described above is the purse-string suture that may be utilized to gather and attach the visceral pleura 1101 around the conduit 1204 or other device to create the seal. While this technique and other similar techniques may be utilized to create a seal, when the suture is pushed through the visceral pleura 1101 and around the conduit 1204, it will inevitably leave small holes or tears through the pleura which may eventually lead to leaks. Accordingly, it would be advantageous to seal the visceral pleura 1101 around the conduit 1204 without having to make any holes or tears through or in the visceral pleura 1101. If the visceral pleura 1101 were to be gathered around the conduit or other device, it would provide the accessibility to use a ring-type device to secure the gathered pleura around the conduit or other medical device.

Figure 13A:
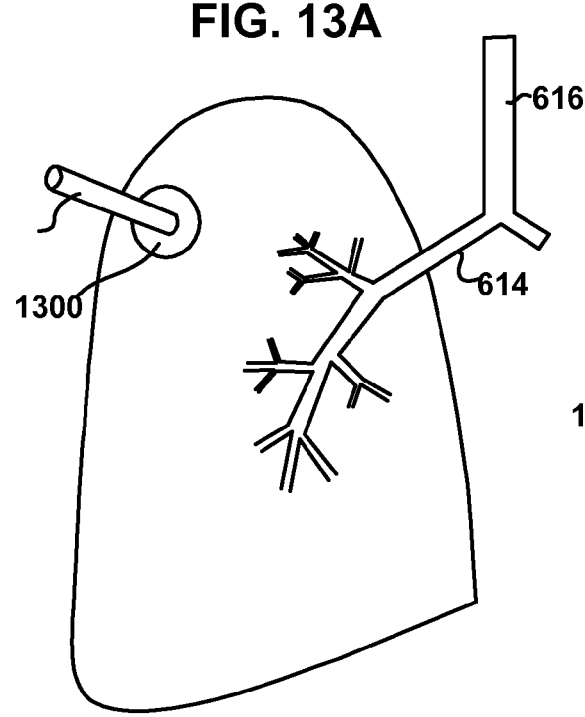
FIGS. 13A and 13B are diagrammatic representations of an exemplary visceral pleura ring connector in accordance with the present invention.
Figure 13B:
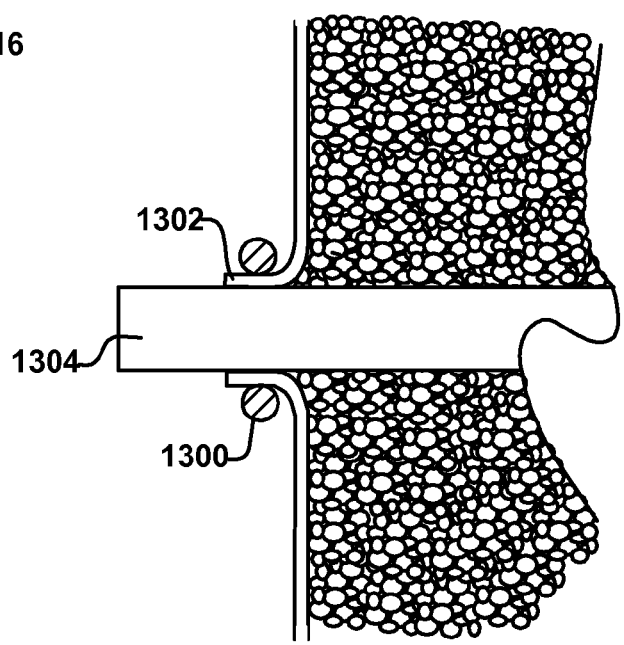

Referring to FIGS. 13A and 13B, there is illustrated an exemplary visceral pleural ring connector 1300 in accordance with the present invention. As illustrated, the visceral pleural ring connector 1300 is simply placed around the gathered pleura 1302 which is gathered around the conduit 1304. Any suitable biocompatible material may be utilized in constructing the visceral pleural ring connector 1300. The visceral pleural ring connector 1300 may be constructed from any number of suitable materials, including superelastic materials such as nickel titanium alloys and bioabsorbable materials such as polyglycolic acid. If a superelastic material, such as a nickel titanium alloy, is utilized, the material may be programmed to be delivered at a first expanded diameter and, when released from a delivery device, allowed to contract to a second smaller diameter that snuggly holds the gathered visceral pleura 1302 to the conduit 1304. It is important that the ring 1300 not fit too tight so as to avoid potential damage to the visceral pleura 1302. Alternately, the ring 1300 may be delivered in its contracted form, expanded and posited over the gathered visceral pleura 1302 and then allowed to contract to its programmed size. In other exemplary embodiments that use other than superelastic materials, various means may be incorporated into the ring structure 1300 for delivery and securing. For example, the ring 1300 may comprise a split ring design wherein the ring 1300 may be opened like a chain link, placed around the gathered visceral pleura and then manually closed to create a snug fit. In other exemplary embodiments, various self-locking structures may be incorporated into the ring structure 1300. For example, a ratchet mechanism may be utilized to tighten the ring 1300 around the gathered visceral pleura 1302. It is important to note that any type of locking or tightening mechanisms may be utilized.

In an alternate exemplary embodiment, one or more agents may be affixed to the ring 1300. The one or more agents may be directly affixed to the surface of the ring 1300, incorporated into a polymeric vehicle and then affixed to the surface of the ring 1300, incorporated into channels or holes in the ring 1300 or incorporated into the bulk material forming the ring 1300. The one or more agents may include chemicals to promote the pleurodesis reaction between the parietal pleura (inner thoracic wall) and the visceral pleura (lung). The pleurodesis is a key component to the chronic success of the procedure. The pleurodesis reaction will allow for the anastomosis to chronically exist without the danger of pneumothorax.

In accordance with another exemplary embodiment, a pulmonary visceral pleura anastomosis reinforcement device may be utilized to create a strong and air tight seal around a conduit of other device posited in the lung through a non-native airway. As described above, when a suture is passed through the visceral pleura and around the conduit, it will inevitably leave small holes or tears through the pleura which may lead to leaks. However, the advantage of the purse-string suture is the ability for the conduit or other device to be removed from the anastomosis even after the suture has been secured. The pulmonary visceral pleura anastomosis reinforcement device may be positioned around the conduit or other device prior to making the purse-string suture thereby reducing the likelihood of a suture hole or tear leading to leaks and potentially a pneumothorax.

Figure 14:
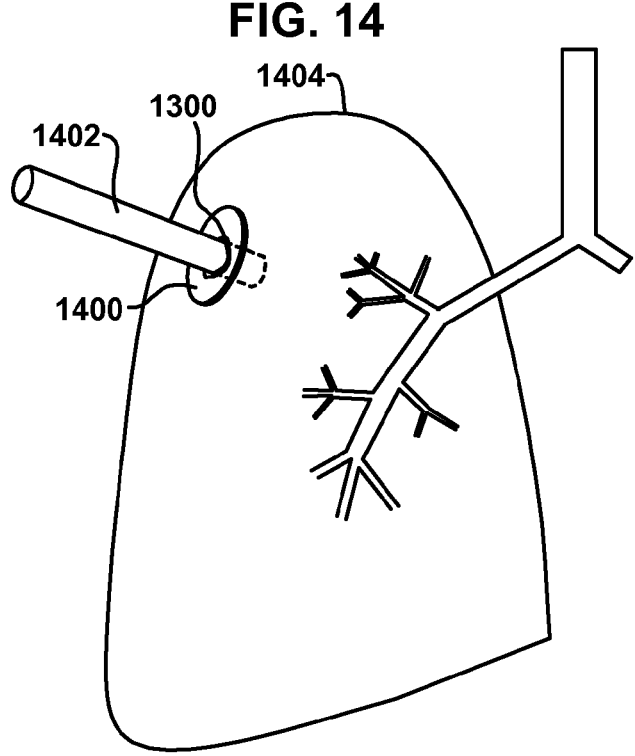
FIG. 14 is a diagrammatic representation of an exemplary pulmonary visceral pleura anastomotic reinforcement device in accordance with the present invention.

Referring to FIG. 14, there is illustrated an exemplary pulmonary visceral pleura anastomosis device 1400 in accordance with the present invention. As illustrated, the pulmonary visceral pleura anastomosis reinforcement device 1400 fits around the conduit 1402 or other medical device. When in position, the visceral pleura 1404 and the pleura anastomosis reinforcement device 1400 are gathered and sutured or secured with the ring described above. Although shown as a substantially circular disc, the reinforcement device 1400 may comprise any suitable shape or configuration that lends itself to the process described herein.

The pulmonary visceral pleura anastomosis reinforcement device 1400 may be a removable device or a permanent implant. The reinforcement device 1400 may be sutured in place, stapled into place, affixed in place with a tissue adhesive or any other suitable means. In addition, the reinforcement device may be combined with a tissue growth factor to promote endothelialization.

The pulmonary visceral pleura anastomosis reinforcement device 1400 may be fabricated from any number of biocompatible materials, including metals, metal alloys and polymers. The material may be biodegradable, for example, polyglycolic acid or non-biodegradable, for example Teflon®. In addition, the material may comprise animal tissue. Currently, materials exist that prevent leaks from occurring where tissue is resected from the lungs. A number of various materials, including Teflon® are currently being utilized. However, in the present invention, the material is formed into a structure for the acute reinforcement around a bypass anastomosis to prevent any leakage.

One or more agents may be affixed to the reinforcement device 1400. The one or more agents may be directly affixed to the surface of the reinforcement device 1400, incorporated into a polymeric vehicle and then affixed to the surface of the reinforcement device 1400, incorporated into channels or holes in the reinforcement device 1400. The one or more agents may include chemicals to promote the pleurodesis reaction between the parietal pleura (inner thoracic wall) and the visceral pleura (lung). The pleurodesis is a key component to the chromic success of the procedure. The pleurodesis reaction will allow for the anastomosis to chronically exist without the danger of pneumothorax.

The above-described devices are utilized to treat the symptoms of chronic obstructive pulmonary disease by applying the theory of collateral ventilation. The devices would provide trapped air in the lung to escape through an alternate pathway through the pleura of the lung. In order for these devices to be effective, the conduits should preferably remain patent throughout the lifetime of the implant. Because the body reacts to implants by building tissue barriers around the device, the patency of the implant may come into question. Accordingly, the present invention relates to a device that allows all previously described devices to remain patent once implanted into the lung parenchyma. Tissue growth at the tip of the conduit or other device is hindered or inhibited mechanically or chemically. By doing this, one could ensure that the lumen of the implant remains patent thereby allowing air from the lung to move freely through the device.

Exemplary mechanical embodiments of the present invention may include features attached to or part of the implanted device or independent devices used as accompaniments to the implant, for example, introduced periodically utilizing interventional techniques. For example, as illustrated in FIG. 15, a serrated tip 1502 may be formed at or attached to the conduit or implant 1504. FIG. 15 shows conduit or implant 1504 passing through thoracic wall 1500 between two ribs 1501 into parenchymal tissue 1506. The serrated tip 1502 could hinder the growth of tissue by constantly creating new injury due to implant device 1504 movement relative to the surrounding lung parenchymal tissue 1506.

In an exemplary stand-alone embodiment, as illustrated in FIG. 16, a trocar 1602 may be inserted through the lumen of the implant 1604 to inhibit tissue growth at the tip of the implant 1604. Essentially, trocar 1602 is a sharp pointed or sharp tipped surgical instrument used with a cannula to puncture a body cavity. In this case, however, the trocar is adopted to create an opening in tissue ingrowth.

In an alternate exemplary embodiment a modified balloon catheter 1702, as illustrated in FIG. 17, may be utilized within the lumen of the implant 1704. The balloon 1706 may be repeatedly inflated and deflated just beyond the tip of the implant to inhibit tissue growth.

Each of these independent devices may be used periodically on a consistent basis for as long as the implant remains in the body.

Tissue growth hindrance or inhibition may also be achieved through the application of certain drugs. For example, as illustrated in FIG. 18, the implanted device 1802 may be coated at or near the tip with a drug or agent 1804 that inhibits cell growth. The drug or agent 1804 may be affixed to the implant 1802, incorporated directly into the implant 1802 or incorporated into a polymeric matrix and then affixed to the implant 1802. Alternatively, a cuff or other similar device may be utilized to incorporate the drug or agent. Regardless of the particular configuration, the drug or agent 1804 should be configured for sustained release over a given time period. In addition, the drug delivery vehicle may be configured to be refilled periodically through any number of known means, for example, via an injection catheter.

In yet another alternate exemplary embodiment, a drug or agent may be injected locally through the lumen of the device as illustrated in FIG. 19. As illustrated, a device such as an injection catheter 1906 or infusion balloon may be guided through the lumen of the implant 1902 and deliver the agent or drug 1904 directly to the site. Depending upon the agency and or chemical, one or more applications may be required. Any number of agents or drugs may be utilized, for example, a rapaymcin or elastic may be utilized.

While exemplary embodiments of the invention have been described with respect to the treatment of tissue in-growth and related complications, it is important to note that the local delivery of drug/drug combinations may be utilized to treat a wide variety of conditions utilizing any number of medical devices, or to enhance the function and/or life of the device. For example, intraocular lenses, placed to restore vision after cataract surgery is often compromised by the formation of a secondary cataract. The latter is often a result of cellular overgrowth on the lens surface and can be potentially minimized by combining a drug or drugs with the device. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators can also benefit from the device-drug combination approach. Devices which serve to improve the structure and function of tissue or organ may also show benefits when combined with the appropriate agent or agents. For example, improved osteo-integration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this drug-device combination approach. Perivascular wraps may be particularly advantageous, alone or in combination with other medical devices. The perivascular wraps may supply additional drugs to a treatment site. Essentially, any type of medical device may be coated in some fashion with a drug or drug combination which enhances treatment over use of the singular use of the device or pharmaceutical agent.

In addition to various medical devices, the coatings on these devices may be used to deliver therapeutic and pharmaceutical agents including: anti-proliferative/anti-mitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

In accordance with yet another alternate exemplary embodiment, variable parietal/visceral pleural couplings may be utilized for the placement of conduits or other implantable devices into the lung through non-native airways without the need for the creation of a pleurodesis or localized pleurodesis. In addition, the variable parietal/visceral pleural coupling would allow independent motion of the visceral and parietal pleura without compromising pressures in the thoracic cavity.

Developing a localized fibrotic adhesion between the lung and the inner thoracic wall may be difficult due to the dynamic movement between the two surfaces. Additionally, a small localized area may create a stress concentration area that would lead to a tear in the lung pleura that may potentially cause a pneumothorax. Finally, the adhesion of the surface of the lung may prevent the lung from being fully emptied during exhalation. The present invention overcomes these potential difficulties.

Figure 20:
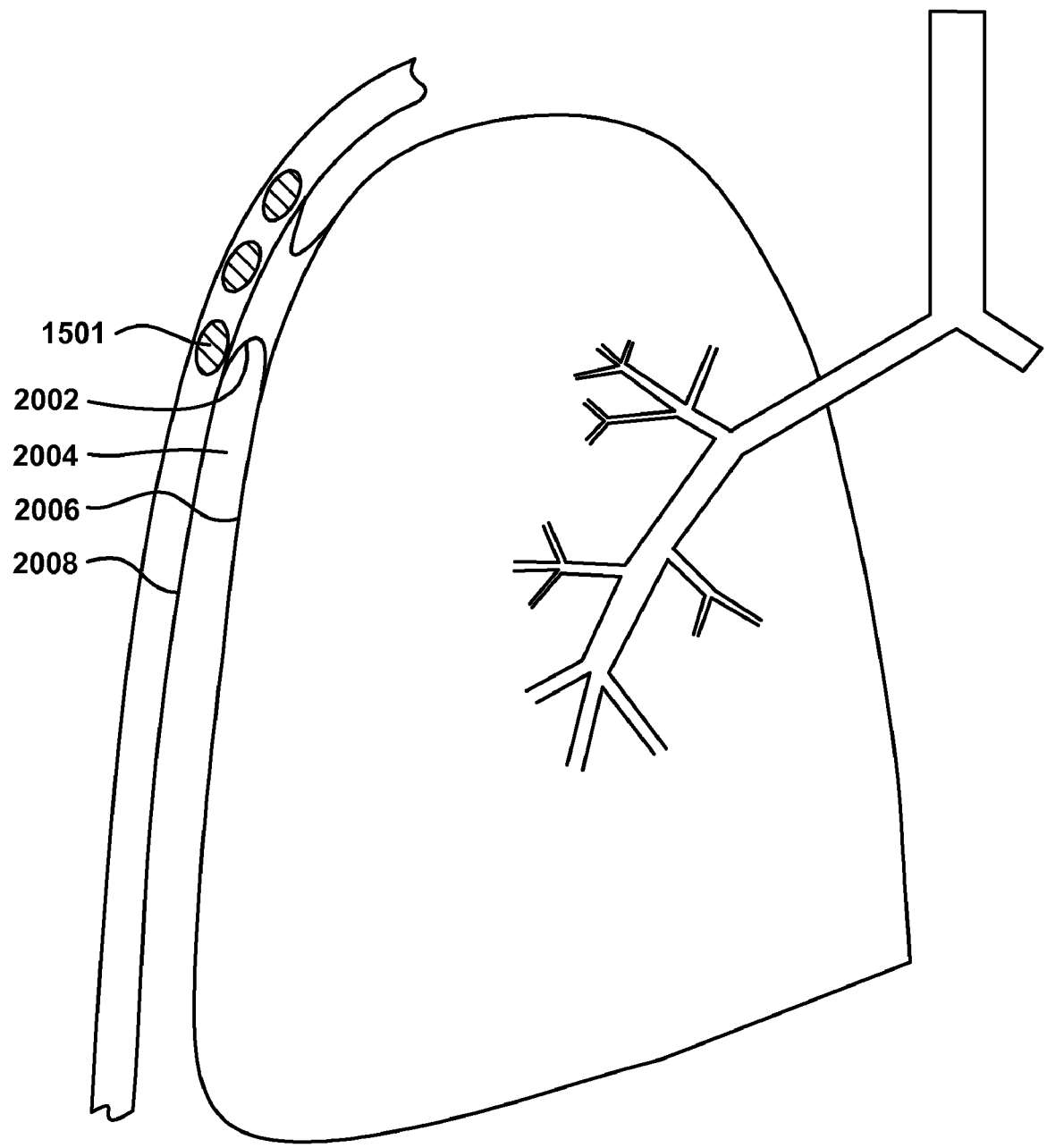
FIG. 20 is a diagrammatic representation of a first exemplary variable parietal/visceral pleural coupling in accordance with the present invention.

Referring now to FIG. 20, there is illustrated a first exemplary embodiment of a variable parietal/visceral pleura coupling in accordance with the present invention. In this exemplary embodiment, the device comprises a rolling membrane coupling 2002. As illustrated, the rolling membrane coupling 2002 comprises a toroidal shape and is positioned in the pleural cavity 2004 and affixed to both the visceral pleura 2006 and the parietal pleura 2008. The rolling membrane coupling 2002 may be attached to both the visceral pleura 2006 and the parietal pleura 2008 by any suitable means, including sutures and adhesives. The toroidal shape allows for flexible movement between the two pleurae. Once the rolling membrane coupling 2002 is in place, a conduit or other device as described herein may be implanted.

Figure 21:
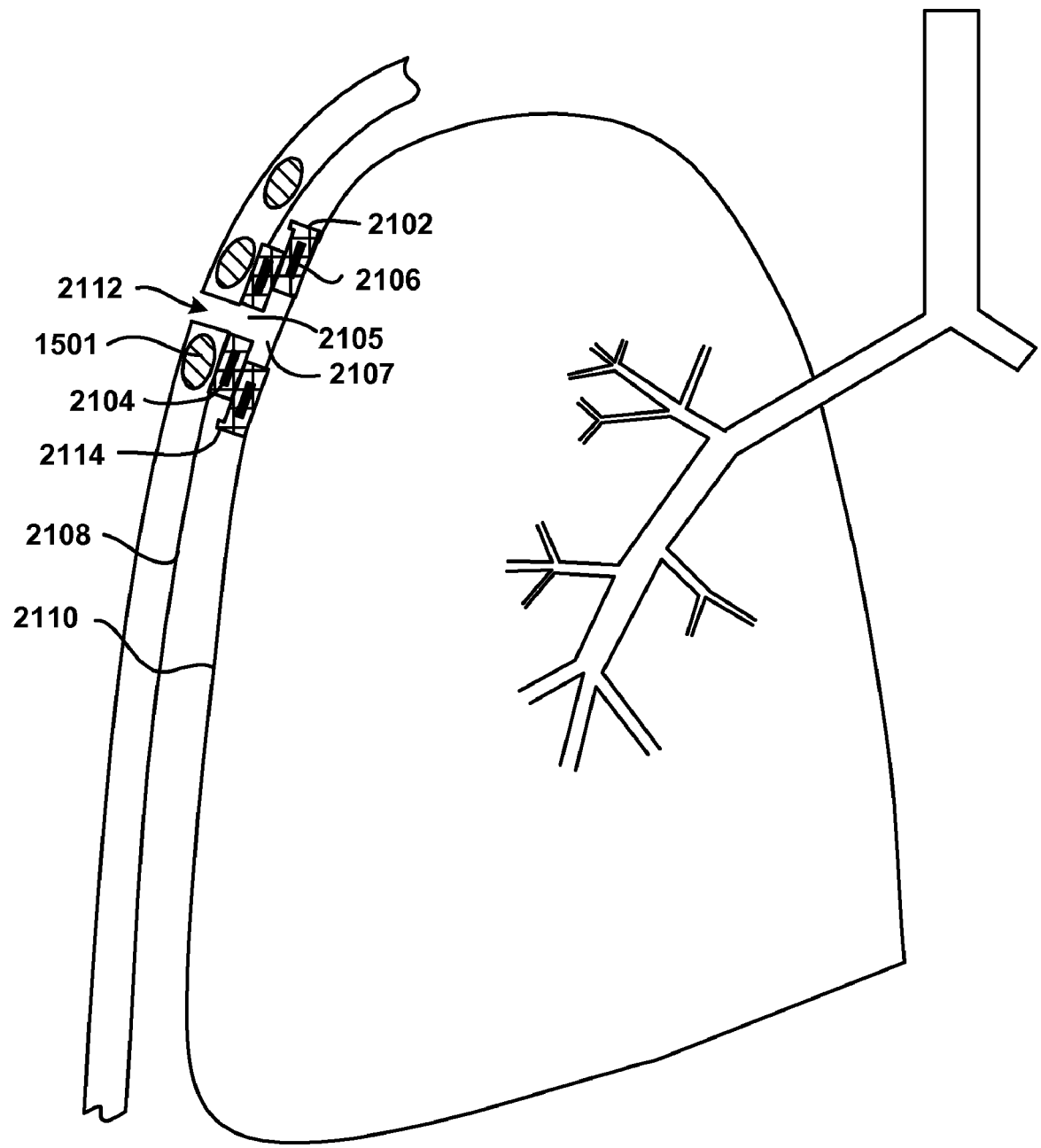
FIG. 21 is a diagrammatic representation of a second exemplary variable parietal/visceral pleural coupling in accordance with the present invention.

FIG. 21 illustrates a second exemplary embodiment of a variable parietal/visceral pleura coupling in accordance with the present invention. In this exemplary embodiment a magnetic coupling device 2102 is utilized to create the seal. As illustrated, one magnet 2104 is attached to the parietal pleura 2108 and a second magnet 2106 is attached to the visceral pleura 2110. The magnets 2104 and 2106 may comprise any suitable size and shape defining an opening 2112 for the placement of the conduit or other medical device. The magnets 2104 and 2106 may comprise any suitable magnetic material that is biocompatible. The magnets 2104 and 2106 may be attached to the pleura 2108, 2110 utilizing any suitable techniques such as adhesives. A seal is maintained using the magnets 2104 and 2106 to maintain surface contact during independent movement of the coupling 2102 and pleura 2108, 2110. At least one magnet 2106 may comprise a lip or ledge 2114 to prevent the magnets from 2104, 2106 sliding too far and moving out of alignment. As illustrated, the opening 2107 in the magnet 2106 attached to the visceral pleura 2110 is larger than the other opening 2105 to account for relative movement.

Figure 22:
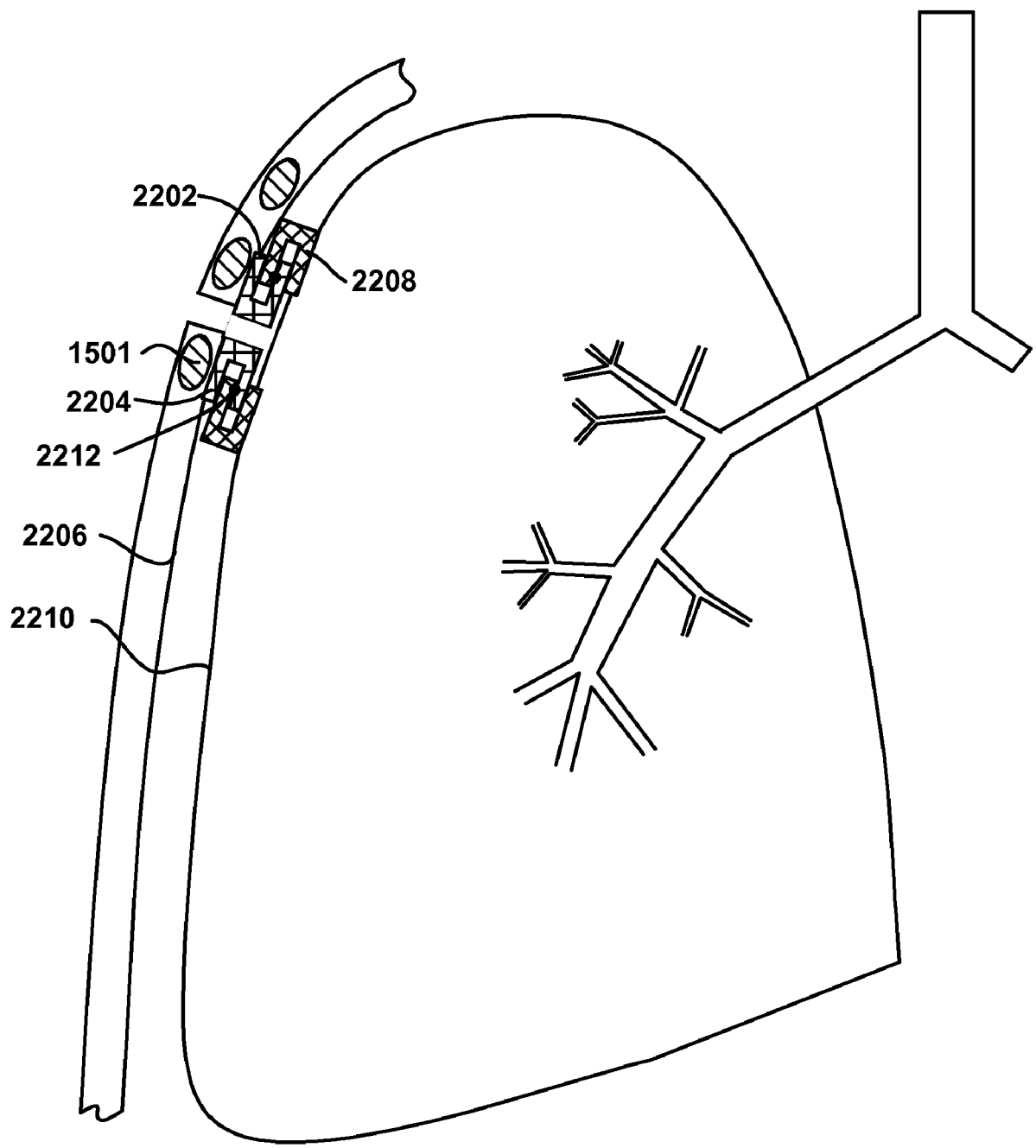
FIG. 22 is a diagrammatic representation of a third exemplary variable parietal/visceral pleural coupling in accordance with the present invention.

FIG. 22 illustrates a third exemplary embodiment of a variable parietal/visceral pleura coupling in accordance with the present invention. In this exemplary embodiment a compression seal coupling 2202 is utilized to maintain the seal. A first coupling component 2204 is attached to the parietal pleura 2206 using any suitable means and a second coupling component 2208 is attached to the visceral pleura 2210 using any suitable means. A seal 2212 such as an o-ring may be incorporated to ensure the integrity of the seal between the first and second components 2204, 2208.

Figure 23:
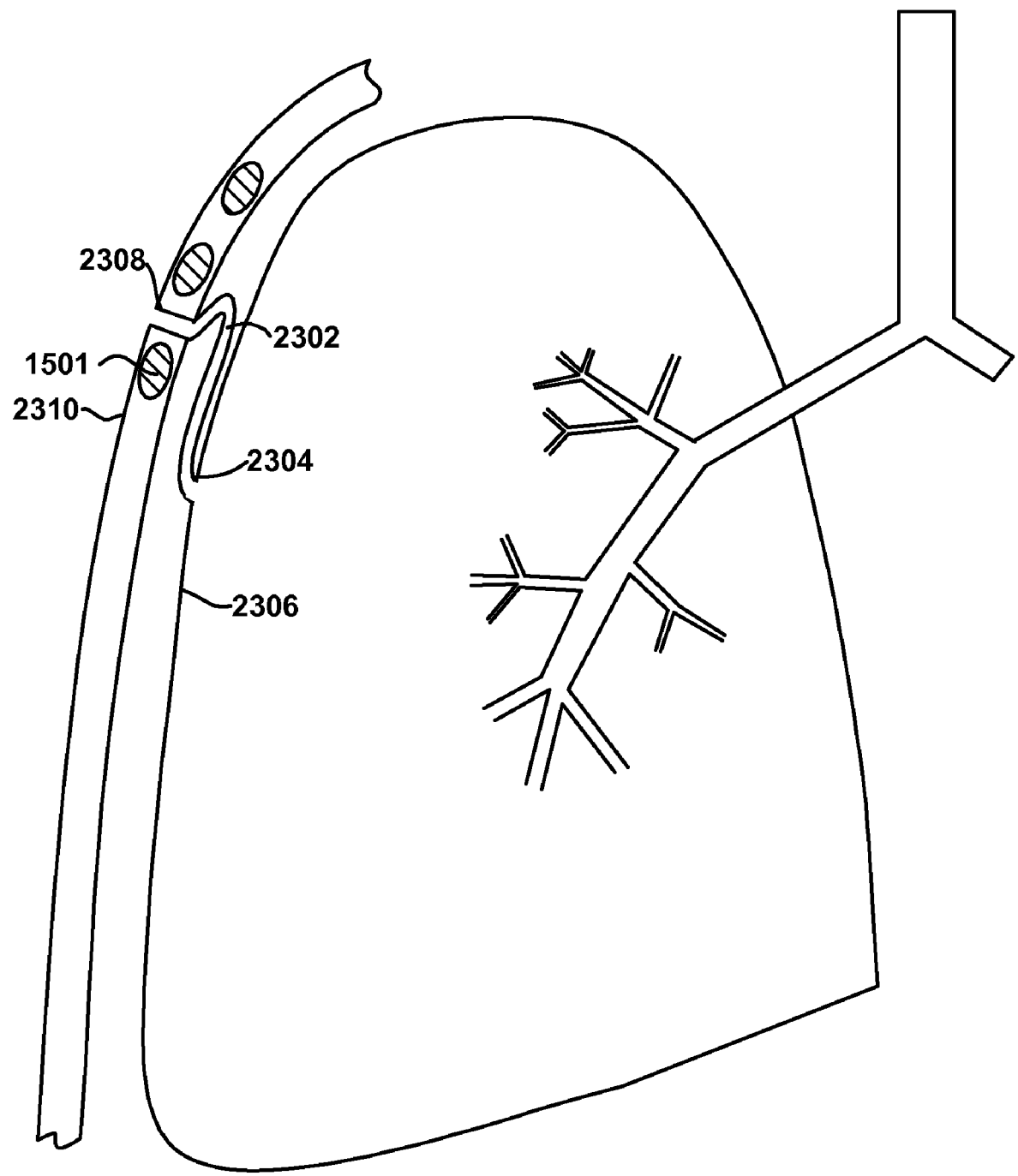
FIG. 23 is a diagrammatic representation of a fourth exemplary variable parietal/visceral pleural coupling in accordance with the present invention.

FIG. 23 illustrates a fourth exemplary embodiment of a variable parietal/visceral pleura coupling in accordance with the present invention. In this exemplary embodiment, a tube coupling 2302 is utilized to create the seal. One end 2304 of the tube 2302 is attached to the visceral pleura 2306 of the lung while the other end 2308 of the tube 2302 is attached to the skin 2310 of the patient.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A pleural cavity coupling comprising:
a first section that defines a first lumen having a first longitudinal axis, said first section adapted to be sealed to a parietal pleura;
a second section that defines a second lumen having a second longitudinal axis, said second section adapted to be sealed to the visceral pleura;
at least one of an adhesive and a suture adapted to secure the second section to the visceral pleura;
said first lumen of the first section in air-tight communication with the second lumen of the second section;
wherein the first section and the second section are moveable relative to each other and wherein the first lumen is sealed to the second lumen such that the communication between the first lumen and the second lumen remains sealed and air-tight as the first section moves relative to the second section; and
whereby the pleural cavity coupling is adapted to allow gasses to flow from a lung of a patient across the pleural cavity without causing a pneumothorax.

2. The coupling of claim 1 including:
the first and second sections defining a compression seal coupling in order to maintain the air-tight communication.

3. The pleural cavity coupling of claim 2 including:
said compression seal coupling includes an o-ring.

4. The pleural cavity coupling of claim 1, wherein:
said first section includes a first circular slot and a first rim;
said second section includes a second circular slot and a second rim;
wherein the first rim is received in the second circular slot and the second rim is received in the first circular slot; and
an o-ring located between the first rim and said second rim to maintain the air-tight communication.

5. The pleural cavity coupling of claim 1 adapted to establish a pleurodesis free connection between the parietal pleura and the visceral pleura.

6. The pleural cavity coupling of claim 1 wherein said first section and said second section together comprise a toroidal shape.

7. The pleural cavity coupling of claim 1 wherein said first section and said second section together comprise a rolling membrane.

8. The pleural cavity coupling of claim 1 wherein one of said first lumen and said second lumen is larger than the other.

9. The pleural cavity coupling of claim 1 wherein one of said first lumen and said second lumen is larger than the other in order to maintain the air-tight communication as the first section moves relative to the second section.

10. The pleural cavity coupling of claim 1 wherein said first section is in sliding engagement with the second section and the said first lumen is in sliding communication with the second lumen as the first section slides relative to the second section.

11. The pleural cavity coupling of claim 1 wherein said first lumen is in moving air-tight communication with the second lumen as at least one of the first section and the second section move relative to each other.

12. The pleural cavity coupling of claim 1 wherein said first section and said second section are adapted to be in sliding engagement with each other along the direction of the surface of at least one of the parietal pleura and the visceral pleura.

13. A pleural cavity coupling comprising:
a first section that defines a first lumen and the first section is adapted to be in contact with a parietal pleura;
a second section that defines a second lumen and the second section is adapted to be in contact with a visceral pleura;
at least one of an adhesive and a suture adapted to secure the second section to the visceral pleura;
said first lumen of the first section in air-tight communication with the second lumen of the second section;
the first section and the second section are moveable relative to each other such that the communication between the first lumen and the second lumen remains air-tight as the parietal pleura moves relative to the visceral pleura in order to establish a pleurodesis free connection to allow gasses to flow from a lung of a patient across the pleural cavity without causing a pneumothorax.

14. The pleural cavity coupling of claim 13, wherein said first lumen and said second lumen are adapted to create a seal for other devices that are to be implanted into the lung of a patient through the visceral pleura and the parietal pleura.

15. The pleural cavity coupling of claim 13, wherein the first section and second section together define a compression seal coupling.

16. The pleural cavity coupling of claim 15, further comprising an o-ring disposed between the first section and the second section.

17. The pleural cavity coupling of claim 13, wherein:
said first section includes a first circular slot and a first rim;
said second section includes a second circular slot and a second rim; and
wherein the first rim is received in the second circular slot and the second rim is received in the first circular slot.

18. The pleural cavity coupling of claim 17, further comprising an o-ring disposed between the first rim and the second rim.

* * * * *